(12) United States Patent
Liang et al.

(10) Patent No.: US 9,206,431 B2
(45) Date of Patent: Dec. 8, 2015

(54) KIT FOR PRODUCING RECOMBINANT TAG-CLEAVABLE FUSION PROTEINS VIA AT LEAST TWO DIFFERENT EXPRESSION VECTORS ALLOW PROTEIN PRODUCTION IN TWO DIFFERENT SPECIES HOST CELLS

(75) Inventors: Po-Huang Liang, Taipei (TW); Hui-Min Wang, Taipei (TW); Yan-Ping Shih, Gangshan Township, Kaohsiung County (TW)

(73) Assignee: Academia Sinica, Taipei (TW)

( * ) Notice: Subject to any disclaimer, the term of this patent is extended or adjusted under 35 U.S.C. 154(b) by 1320 days.

(21) Appl. No.: 11/862,900

(22) Filed: Sep. 27, 2007

(65) Prior Publication Data

US 2009/0087895 A1 Apr. 2, 2009

(51) Int. Cl.
*C12N 9/50* (2006.01)
*C12N 15/62* (2006.01)
*C12N 15/70* (2006.01)
*C12N 15/81* (2006.01)

(52) U.S. Cl.
CPC ............... *C12N 15/62* (2013.01); *C12N 15/70* (2013.01); *C12N 15/81* (2013.01); *C07K 2319/20* (2013.01); *C07K 2319/21* (2013.01); *C07K 2319/23* (2013.01)

(58) Field of Classification Search
CPC ........... C07K 2319/20; C07K 2319/21; C07K 2319/23; C12N 9/50
See application file for complete search history.

(56) References Cited

U.S. PATENT DOCUMENTS 6,307,038 B1 * 10/2001 Takahashi et al. ........... 536/23.4
6,953,689 B2   10/2005 Clark
7,056,732 B2    6/2006 Hua et al.

OTHER PUBLICATIONS

Wang et al (High-throughput screening of soluble recombinant proteins. In Purifying proteins for proteomics: A laboratory manual (ed. R.J. Simpson), pp. 101-119. Cold Spring Harbor Laboratory Press, Cold Spring Harbor, NY, 2004).*
Kapust et al (Biochemical and Biophysical Research Communications, 294(5): , 28: 949-955, 2002);.*
ATTC-PDF (abstract), Nov. 18, 2011.
Hammarström et al., "Rapid Screening for Improved Solubility of Small Human Proteins Produces as Fusion Proteins in *Escherichia coli*," Protein Sci., 11:313-321 (2002).
Hartley et al., "DNA Cloning Using in Vitro Site-Specific Recombination," Genome Res., 10:1788-1795 (2000).
Shih et al., "High-Throughput Screening of Soluble Recombinant Proteins," Protein Sci., 11:1714-1719 (2002).
Shih et al., "Self-Cleavage of Fusion Protein in Vivo Using TEV Protease to yield native Protein" Protein Science, vol. 14, pp. 936-941. (2005).
van der Heuvel et al., "'Plug and Play'—Expression Systems for High-Quality Production of Recombinant Proteins for Structural Analysis," Gene Funct. Dis., 3(1-2):33-38 (2002).
Walhout et al., "Gateway Recombinant Cloning: Application to the Cloning of Large Numbers of Open Reading Frames or ORFeomes," Methods in Enzymology, 328:575-592 (2000).

* cited by examiner

Primary Examiner — Deborah Crouch
Assistant Examiner — Magdalene Sgagias
(74) Attorney, Agent, or Firm — Wolf, Greenfield & Sacks, P.C.

(57) ABSTRACT

This invention features a kit containing multiple expression vectors for producing tag-cleavable fusion proteins in various expression systems, or for producing fusion proteins in *E. coli* inclusion bodies.

16 Claims, 28 Drawing Sheets

SnaB I: TACGTA

TEV protease: GAGAACCTGTACGTACAGATG

EcoR I: GAATTC

FXa protease: ATCGAGGGAAGG

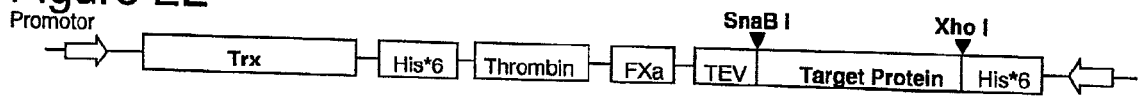
Figure 2L
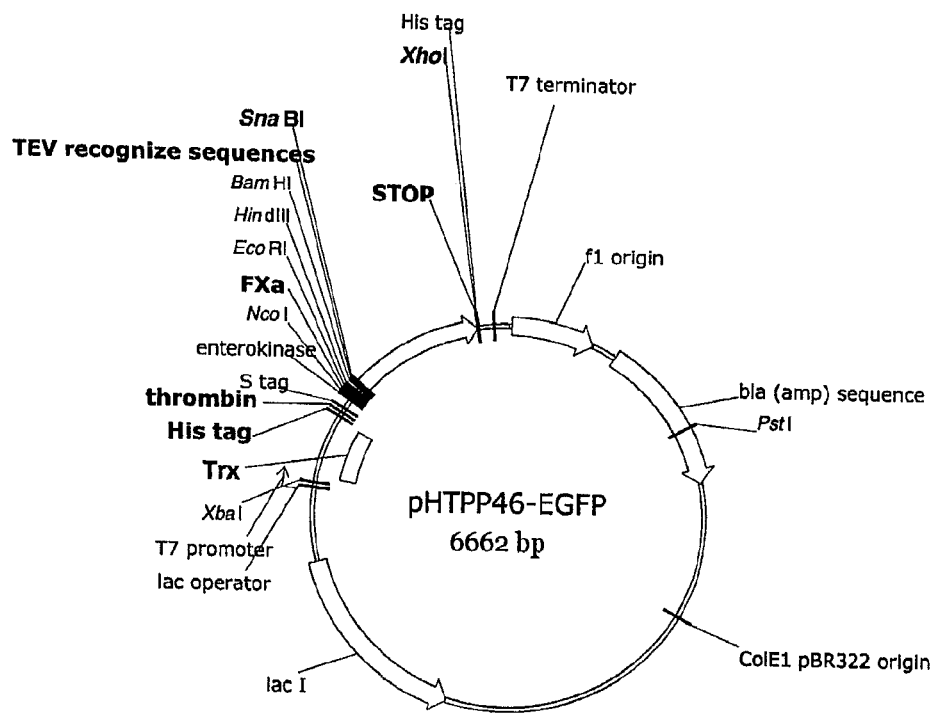

SEQUENCE LISTING

<160> NUMBER OF SEQ ID NOS: 71

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gagaacctgt acgtacag                                                 18

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tatgaagcga cgatggaaaa agaatttc                                      28

<210> SEQ ID NO 3
<211> LENGTH: 26
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 3
tgaagcgacg atggaaaaag aatttc                                         26

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aattcccttc cctcgattct tcccttg                                        27

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cccttccctc gattcttccc ttg                                            23

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aatttcatgg tgagcaaggg cgag                                           24

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
catggtgagc aagggcgag                                                 19

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tcgagtcact tgtacagctc gtccat                                         26

<210> SEQ ID NO 9
<211> LENGTH: 22
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 9
gtcacttgta cagctcgtcc at                                              22

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctagaaataa ttttgtttaa ctttaagaag ga                                   32

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aaataatttt gtttaacttt aagaagag                                        28

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aattcccttc cctcgatacg agctcc                                          26

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cccttccctc gatacgagct cc                                              22

<210> SEQ ID NO 14
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aattcccttc cctcgatgcg acccatttgc tgtccacc                             38

<210> SEQ ID NO 15
<211> LENGTH: 34
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 15
cccttccctc gatgcgaccc atttgctgtc cacc                                    34

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tgcaccacca tcaccatcac agct                                               24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gtgatggtga tggtggtgca agct                                               24

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
aattcccttc cctcgatgat atcagc                                             26

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cccttccctc gatgatatca gc                                                 22

<210> SEQ ID NO 20
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tcgaaggatc cggtggtgag aacctgtacg tacagggagg tggtc                        45

<210> SEQ ID NO 21
<211> LENGTH: 45
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 21
tcgagaccac ctccctgtac gtacaggttc tcaccaccgg atcct         45

<210> SEQ ID NO 22
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
tcgaaaaaag agaggctgaa gctgaattct gcagctcgac gtggcccagc cggccgtctc    60
ggatcggtac g                                                         71

<210> SEQ ID NO 23
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tcgacgtacc gatccgagac ggccggctgg gccacgctcg agctgcagaa ttcagcttca    60
gcctctcttt tt                                                        72

<210> SEQ ID NO 24
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
aattgactag tggggctagc catcatcatc atcatcatat cgagggaagg g             51

<210> SEQ ID NO 25
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
aattcccttc cctcgatatg atgatgatga tgatggctag ccccactagt c             51

<210> SEQ ID NO 26
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tcgaaaaaag agaggctgaa gctgaattct acgtagggct cgagcgtggc ccagccggcc    60
gtctcggatc ggtacg                                                    76

<210> SEQ ID NO 27

```
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
tcgacgtacc gatccgagac ggccggctgg gccacgctcg agccctacgt agaattcagc    60
ttcagcctct cttttt                                                   76

<210> SEQ ID NO 28
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
actagtgggg ctagccatca tcatcatcat catgagaacc tgtac                    45

<210> SEQ ID NO 29
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gtacaggttc tcatgatgat gatgatgatg gctagcccca ctagt                    45

<210> SEQ ID NO 30
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gatccgatgt ccccctatact aggttattgg aaa                                33

<210> SEQ ID NO 31
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
caccctgaaa atacaggttc tcatccgatt ttggaggatg gtc                      43

<210> SEQ ID NO 32
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cgatgtcccc tatactaggt tattggaaa                                      29
```

<210> SEQ ID NO 33
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
aattcaccct gaaatacag gttctcatcc gattttggag gatggtc                47

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
gccggcatag tacgcagctt cttc                                        24

<210> SEQ ID NO 35
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
ttctagaagg tacccgggat ccgcagatcc gcgcccgatg gtgggacg              48

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
gcggatcccg ggtaccttct agaa                                        24

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
atcgatgtct gaattgccgc ccgc                                        24

<210> SEQ ID NO 38
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
gatccgatgt ccctatact aggttattgg aaa                               33

<210> SEQ ID NO 39

```
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tgcagctcga ggaattctcc ctgtacgtac aggttctcat ccgatttttgg aggatggtc    59

<210> SEQ ID NO 40
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cgatgtcccc tatactaggt tattggaaa                                      29

<210> SEQ ID NO 41
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gctcgaggaa ttctccctgt acgtacaggt tctcatccga ttttggagga tggtc         55

<210> SEQ ID NO 42
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gatccatgtc ccctatacta ggttattgga aa                                  32

<210> SEQ ID NO 43
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
caccctgaaa atacaggttc tcatccgatt ttggaggatg gtc                      43

<210> SEQ ID NO 44
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
catgtcccct atactaggtt attggaaa                                       28

<210> SEQ ID NO 45
<211> LENGTH: 47
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
aattcaccct gaaaatacag gttctcatcc gattttggag gatggtc                  47

<210> SEQ ID NO 46
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
cccttccctc gatatccgat tttggaggat ggtc                               34

<210> SEQ ID NO 47
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
catgtcccct atactaggtt attggaaa                                      28

<210> SEQ ID NO 48
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
aattcccttc cctcgatatc cgattttgga ggatggtc                           38

<210> SEQ ID NO 49
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
tcgaggaatt ctccctgtac gtacaggttc tcatccgatt ttggaggatg gtc          53

<210> SEQ ID NO 50
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
catgtcccct atactaggtt attggaaa                                      28

<210> SEQ ID NO 51
<211> LENGTH: 49
<212> TYPE: DNA
```

<210> SEQ ID NO 51
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
ggaattctcc ctgtacgtac aggttctcat ccgattttgg aggatggtc        49

<210> SEQ ID NO 52
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 52
gatctctgca ggaattcggg gagaacctgt acgtacaggg aggtggtc         48

<210> SEQ ID NO 53
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 53
tcgagaccac ctccctgtac gtacaggttc tccccgaatt cctgcaga         48

<210> SEQ ID NO 54
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 54
tcgagggatc cgatatccac caccaccacc accacc                      36

<210> SEQ ID NO 55
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
gatcggtggt ggtggtggtg gtggatatcg gatccc                      36

<210> SEQ ID NO 56
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 56
tcgacgaatt catggacaaa ttttggactt tc                          32

<210> SEQ ID NO 57
<211> LENGTH: 28
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 57
cgaattcatg gacaaatttt ggactttc                                            28

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
tcgaggtgac tgtgagcctc gtg                                                 23

<210> SEQ ID NO 59
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ggtgactgtg agcctcgtg                                                      19

<210> SEQ ID NO 60
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
tatgccggat tattcatacc gtc                                                 23

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
tgccggatta ttcataccgt c                                                   21

<210> SEQ ID NO 62
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
tcgagatacg ccggaccagt gaac                                                24

<210> SEQ ID NO 63
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 63
gatacgccgg accagtgaac                                                    20

<210> SEQ ID NO 64
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ggccgcgaat tcttaattaa acatatg                                            27

<210> SEQ ID NO 65
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gcgaattctt aattaaacat atg                                                23

<210> SEQ ID NO 66
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gtcatgtttg acagcttat                                                     19

<210> SEQ ID NO 67
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
aattgtcatg tttgacagct tat                                                23

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
gagaacctgt acgtacagat g                                                  21

<210> SEQ ID NO 69
<211> LENGTH: 18
<212> TYPE: DNA
<213> ORGANISM: Artificial Sequence
<220> FEATURE:
<223> OTHER INFORMATION: Description of Artificial Sequence: Synthetic
```

```
                                          oligonucleotide

<400> SEQUENCE: 69
atcgagggaa gggaattc                                                      18

<210> SEQ ID NO 70
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
atcgagggaa gg                                                            12

<210> SEQ ID NO 71
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 71

His His His His His His
1               5
```

KIT FOR PRODUCING RECOMBINANT TAG-CLEAVABLE FUSION PROTEINS VIA AT LEAST TWO DIFFERENT EXPRESSION VECTORS ALLOW PROTEIN PRODUCTION IN TWO DIFFERENT SPECIES HOST CELLS

BACKGROUND OF THE INVENTION

A target polypeptide can be prepared by expressing a fusion protein including the target polypeptide and a protein tag that improves protein expression and facilitates protein purification. The protein tag can be removed by protease cleavage. A target polypeptide thus prepared, however, may be inactive due to possible addition of terminal amino acid residues.

Different expression systems might be needed for preparation of different target polypeptides. For example, glycopolypeptides are preferred to be expressed in mammalian cells, which possess glycosylation machinery. As another example, polypeptides toxic to mammalian cells can only be expressed in non-mammalian expression systems. Therefore, a single expression system is not sufficient for producing a large variety of target polypeptides.

SUMMARY OF THE INVENTION

The present invention provides a kit containing multiple expression vectors for producing tag-cleavable fusion proteins in various expression systems, or a vector for producing fusion proteins in E. coli inclusion bodies. The multiple expression vectors can be categorized into two groups; namely, one for high-efficient cloning of a target gene, and the other for producing a sequence-specific target polypeptide (i.e., having the exact amino acid sequence encoded by a target gene).

In one aspect, this invention features a kit containing 2-6 expression vectors, at least two of which allow protein production in two different expression systems, such as an E. coli system, a yeast system (e.g., a pichica system), a baculovirus system, a mammalian cell system, or a cell-free system. Each of the expression vectors includes a first portion encoding a protein tag, and a second portion containing a nucleotide sequence that encodes a protease recognition site and includes one or two restriction sites identical in all of the 2-6 expression vectors. A fusion protein expressed therefrom include the protein tag, the protease recognition site, and the target polypeptide encoded by the target gene. Upon protease cleavage at the protease recognition site, the target polypeptide separates from the protein tag.

Any protein tag commonly used in expressing tag-fused proteins can be employed in the vectors described above. Exemplary tags include but are not limited to hexa-His (SEQ ID NO: 71), Maltose binding protein (MBP), N-utilizing substance A (NusA), thioredoxin, calmodulin-binding protein (CBP), glutathione S-transferase (GST), and α-factor.

A protease recognition site is a particular amino acid sequence recognizable by a protease, which cleaves within this sequence. Any commonly used protease recognition site can be employed in the vectors described above. Examples include but are not limited to the recognition sites of thrombin, Factor Xa (FXa), and tobacco etch virus (TEV) protease.

In one example, the kit of this invention contains 2-6 expression vectors, each of which includes the cloning sites of EcoR I and Xho I. These vectors can include a nucleotide sequence that encodes the recognition site of FXa. See FIG. 1, bottom panel. Such vectors include pHTPP10, pHTPP11 (or pHTPP11-EGFP), pHTPP12, pHTPP13, pHTPP14, pHTPP15, pHTPY2, pHTPBV5, pHTPM3, pHTPM6, and pHTPC1. They can also include a nucleotide sequence that encodes the recognition site of TEV protease. Such vectors include pHTPBV1, pHTPBV2, and pHTPBV4.

In another example, the kit of this invention contains 2-6 expression vectors, each of which includes the nucleotide sequence of GAGAACCTGTACGTACAG (SEQ ID NO: 1) (encoding the TEV protease recognition site and including an SnaB I site for cloning a target gene). A fusion protein expressed from this vector can yield, upon TEV protease cleavage, a polypeptide having the exact amino acid sequence encoded by a target gene that contains its own stop codon. See FIG. 1, top panel. Examples of these vectors include pHTPP41, pHTPP42, pHTPP43, pHTPP44, pHTPP45, pHTPP46, pHTPY4, pHTPBV3, pHTPBV6, pHTPM5, and pHTPM7.

The kit as described above can further includes an expression vector for producing a fusion protein in inclusion bodies in E. coli. This fusion protein includes a target protein and a protein carrier, such as ketosteroid isomerase (KSI) and polyhedron, which facilitates translocation of the fusion protein to inclusion bodies in E. coli. Examples include pHTPI2, pHTPI2-EGFP, pHTPI3, and pHTPI3-EGFP.

All of the above-mentioned kits can be combined with each other to form additional new kits, which are also within the scope of this invention.

In another aspect, the present invention provides a kit containing a first vector set including two expression vectors as described above, both allowing production of tag-cleavage fusion proteins in a first expression system. Further, the first vector of this set includes one or two efficient cloning sites (e.g., EcoR I and Xho I) and the second vector includes the nucleotide sequence that encodes the TEV protease recognition site and includes an SnaB I site for cloning a target gene. These two expression vectors can include nucleotide sequences that encode a same protein tag. Exemplary sets of vectors contained in this kit include but are not limited to pHTPP10 and pHTPP41, pHTPP11 and pHTPP42, pHTPP12 and pHTPP43, pHTPP13 and pHTPP44, pHTPP14 and pHTPP45, pHTPP15 and pHTPP46, pHTPY2 and pHTPY4, and pHTPM3 or pHTPM6 and pHTPM5 or pHTPM7. As another example, one vector in the kit is pHTPBV1, pHTPBV2, pHTPBV4, or pHTPBV5; and the other is pHTPBV3 or pHTPBV6.

This kit can include a second set of two expression vectors as described above. This expression vector set allows protein expression in an expression system different from the first expression system. Similar to the first set, the second set includes one vector that has one or two efficient cloning sites (e.g., EcoR I and Xho I) and the other vector that contains the nucleotide sequence encoding the TEV protease recognition site and including an SnaB I site for cloning a target gene. The two expression vectors can include nucleotide sequences that encode the same protein tag.

Other features or advantages of the present invention will be apparent from the following drawings and detailed description of several embodiments, and also from the appending claims.

DETAILED DESCRIPTION OF THE INVENTION

The present invention features a kit containing any combination of the expression vectors described herein for expressing tag-cleavable fusion proteins in various expression systems, or for expression fusion proteins in inclusion bodies.

Figure 1:
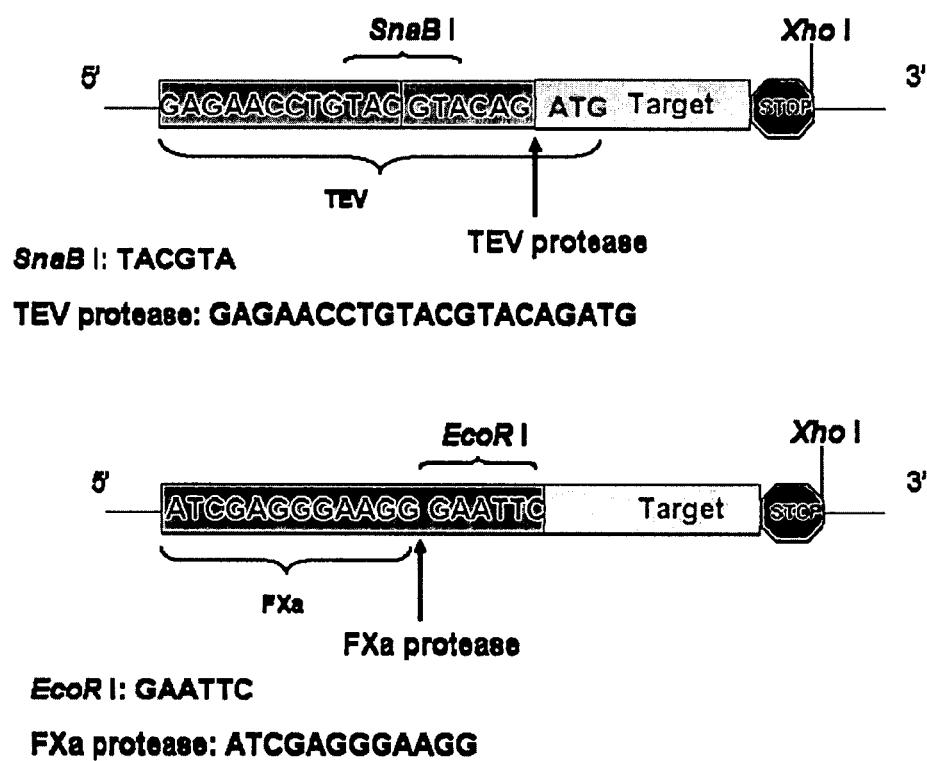
FIG. 1 is a diagram showing the linkage between a nucleotide sequence that encodes a protease recognition site and a restriction site for cloning a target gene. Top panel: the nucleotide sequence encoding a TEV protease recognition site and including an SnaB I site (SEQ ID NO: 68); the arrow indicates where TEV protease cleaves. Bottom panel: linkage between the nucleotide sequence encoding an FXa recognition site and an EcoR I cloning site; the arrow indicates where FXa cleaves (SEQ ID NOS 69 & 70 respectively in order of appearance).

Expression vectors, designed for producing tag-cleavable fusion proteins, include the following features: (1) a first nucleotide sequence that encodes a first protein tag, (2) a second nucleotide sequence that encodes a first protease recognition site, and (3) one or two sites (e.g., EcoR I, Bam HI, Hind III, Xho I, and Xba I) for cloning a target gene. The second nucleotide sequence is located between the first nucleotide sequence and one cloning site. It adjoins or overlaps with one cloning site. In one example, the second nucleotide sequence is GAGAACCTGTACGTACAG (SEQ ID NO: 1), which encodes the TEV protease recognition site and includes an SnaB I site (underlined) for cloning a target gene. See FIG. 1, top panel. An expression vector including this sequence provides the advantage that, after TEV protease cleavage, a fusion protein expressed therefrom yields a polypeptide having the exact amino acid sequence encoded by a target gene. See U.S. patent application Ser. No. 11/364, 716. In another example, the second nucleotide sequence, adjoined an EcoR I site, encodes the FXa recognition site. See FIG. 1, bottom panel. Note that EcoR I site is highly efficient for cloning target genes and FXa is a cheap protease.

The vectors can further include a third nucleotide sequence encoding a second protein tag, which is different from the first protein tag. Alternatively or in addition, the vectors can include a fourth nucleotide sequence that encodes a second protease recognition site. This nucleotide sequence is located between a nucleotide sequence encoding a protein tag and the nucleotide sequence encoding the first protease recognition site.

An exemplary kit of this invention contains 2-6 expression vectors, all of which include the same cloning site(s). At least two of the vectors allow protein production in two different expression systems. This kit can include 3, 4, 5, or 6 expression vectors, any two of which allow protein production in two different expression systems. One exemplary kit contains 5 expression vectors, (1) a vector selected from pHTPP10, pHTPP11, pHTPP12, pHTPP13, pHTPP14, and pHTPP15; (2) pHTPY2; (3) a vector selected from pHTPBV1, pHTPBV2, pHTPBV4, and pHTPBV5; (4) pHTPM3 or pHTPM6; and (5) pHTPC1. As another example, a kit of this invention contains the following 4 expression vectors: (1) a vector selected from hTPP41, pHTPP42, pHTPP43, pHTPP44, pHTPP45, and pHTPP46; (2) pHTPY4; (3) pHTPBV3 or pHTPBV6; and (4) pHTPM5 or pHTPM7.

As another example, a kit contains one or more vector sets (up to 6), each including two expression vectors as described herein for protein production in the same expression system. One of the two vectors in a set includes two restriction sites (e.g., EcoR I and Xho I) that allow cloning of a target gene with high efficiency. This vector can include any nucleotide sequence that encodes a protease recognition site, e.g., an FXa recognition site. The other vector includes the nucleotide sequence of GAGAACCTGTACGTACAG (SEQ ID NO: 1), which encodes the TEV protease recognition site and an SnaB I site (underlined).

Any of the kits described above can also include an expression vector allowing expression of fusion proteins in *E. coli* inclusion bodies. This vector includes a nucleotide sequence encoding a carrier protein, e.g., KSI or polyhedron. This type of expression vectors is particularly useful for expression a toxic protein as it minimizes the protein's toxicity to host cells.

All of the expression vectors described above can be made by methods well known in the art. In one example, they are prepared by modifying commercially available expression vectors to incorporate the necessary features as described above.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference.

EXAMPLE 1

Figure 2A:
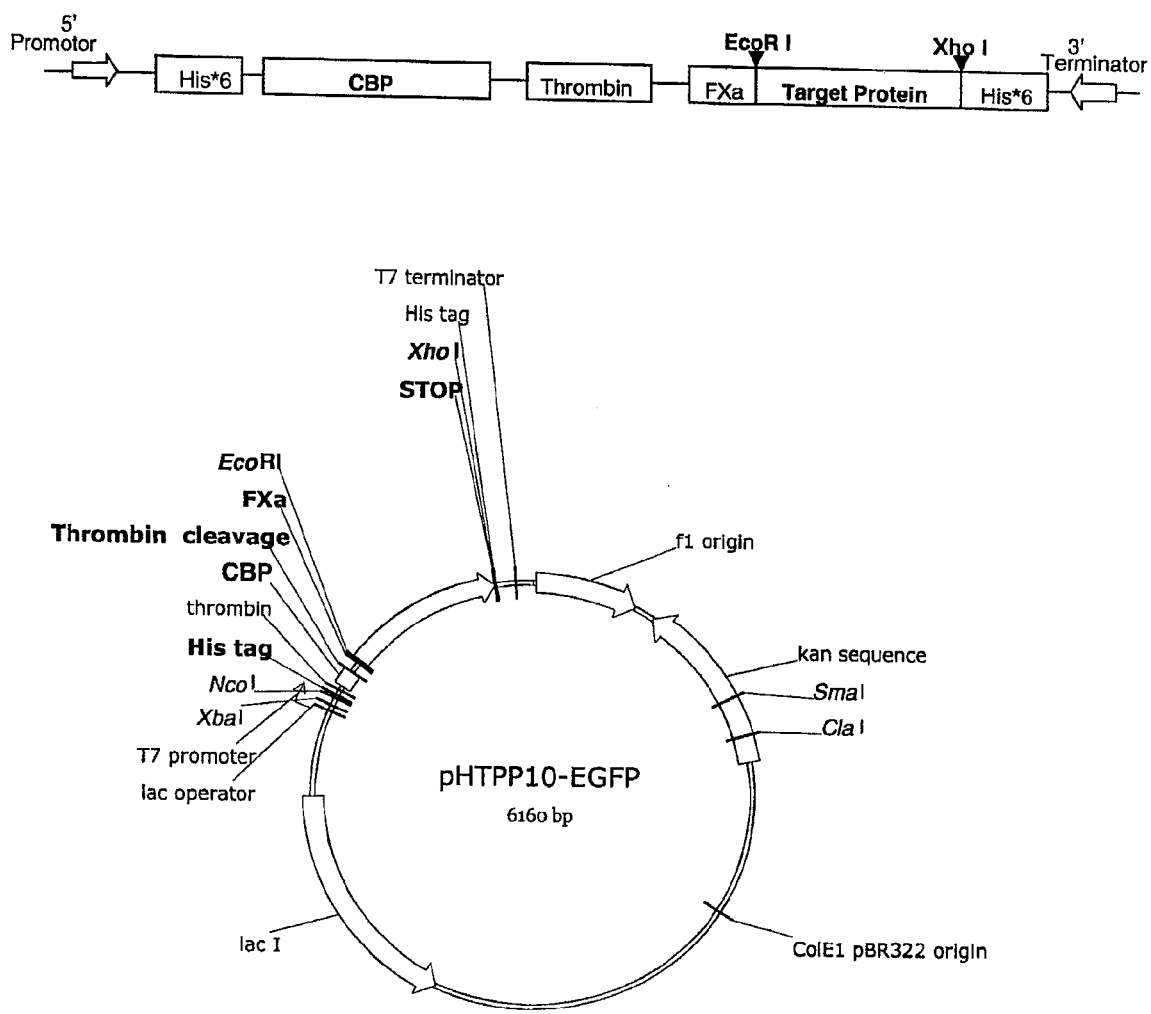
FIG. 2 is a set of maps of expression vectors for protein expression in *E. coli*. A: vector pHTPP10 with Enhanced Green Fluorescent Protein (EGFP) gene cloned therein; B: vector pHTPP11 with EGFP gene cloned therein; C: vector pHTPP12 with EGFP gene cloned therein; D: vector pHTPP13 with EGFP gene cloned therein; E: vector pHTPP14 with EGFP gene cloned therein; F: vector pHTPP15 with EGFP gene cloned therein; G: vector pHTPP41 with EGFP gene cloned therein; H: vector pHTPP42 with EGFP gene cloned therein; I: is a map of expression vector pHTPP43 with EGFP gene cloned therein; J: vector pHTPP44 with EGFP gene cloned therein; K: vector pHTPP45 with EGFP gene cloned therein; and L: vector pHTPP46 with EGFP gene cloned therein (6× His tags disclosed as SEQ ID NO: 71).

Construction of Expression Vectors for Producing Tag-Cleavable Fusion Proteins in *E. coli* Cells Vector pHTPP10 was constructed as follows. Two pairs of primers (1) 5'-TATGAAGCGACGATGGAAAAA-GAATTTC-3' (SEQ ID NO: 2) and 5'-TGAAGCGACGATG-GAAAAAGAATTTC-3' (SEQ ID NO: 3); and (2) 5% AAT-TCCCTTCCCTCGATTCTTCCCTTG-3' (SEQ ID NO: 4) and 5'-CCCTTCCCTCGATTCTTCCCTTG-3 (SEQ ID NO:

5), were used in a sticky-end PCR reaction to amplify the NdeI-CBP-thrombin-FXa-EcoRI cassette from the vector pET-22b(CBP) described in Shih et al., 2002, *Protein Sci.* 11, 1714-1719; and Wang et al, 2004, In *Purifying proteins for proteomics: A laboratory manual* (ed. R. J. Simpson), pp. 111-119. Cold Spring Harbor Laboratory Press, Cold Spring Harbor, N.Y. The resultant PCR products were mixed, denatured, and then renatured to form sticky-end PCT products having the Nde I and EcoR I sites ready for cloning. The DNA fragment thus obtained were then cloned into the NdeI/EcoRI sites of pET-28a(+) to generate pHTPP10 vector. An EGFP gene was amplified from the pEGFP-N2 vector (Clontech) by sticky-end PCR using the primers of 5'-AATTTCATGGT-GAGCAAGGGCGAG-3' (SEQ ID NO: 6) and 5'-CATGGT-GAGCAAGGGCG AG-3' (SEQ ID NO: 7); and 5'-TCGAGT-CACTTGTACAGCTCGTCCAT-3' (SEQ ID NO: 8) and 5'-GTCACTTGTA CAGCTCGTCCAT-3' (SEQ ID NO: 9). The EGFP gene was cloned into pHTPP10 via EcoRI/XhoI sites to produce pHTPP10-EGFP (see FIG. 2A).

Figure 2B:
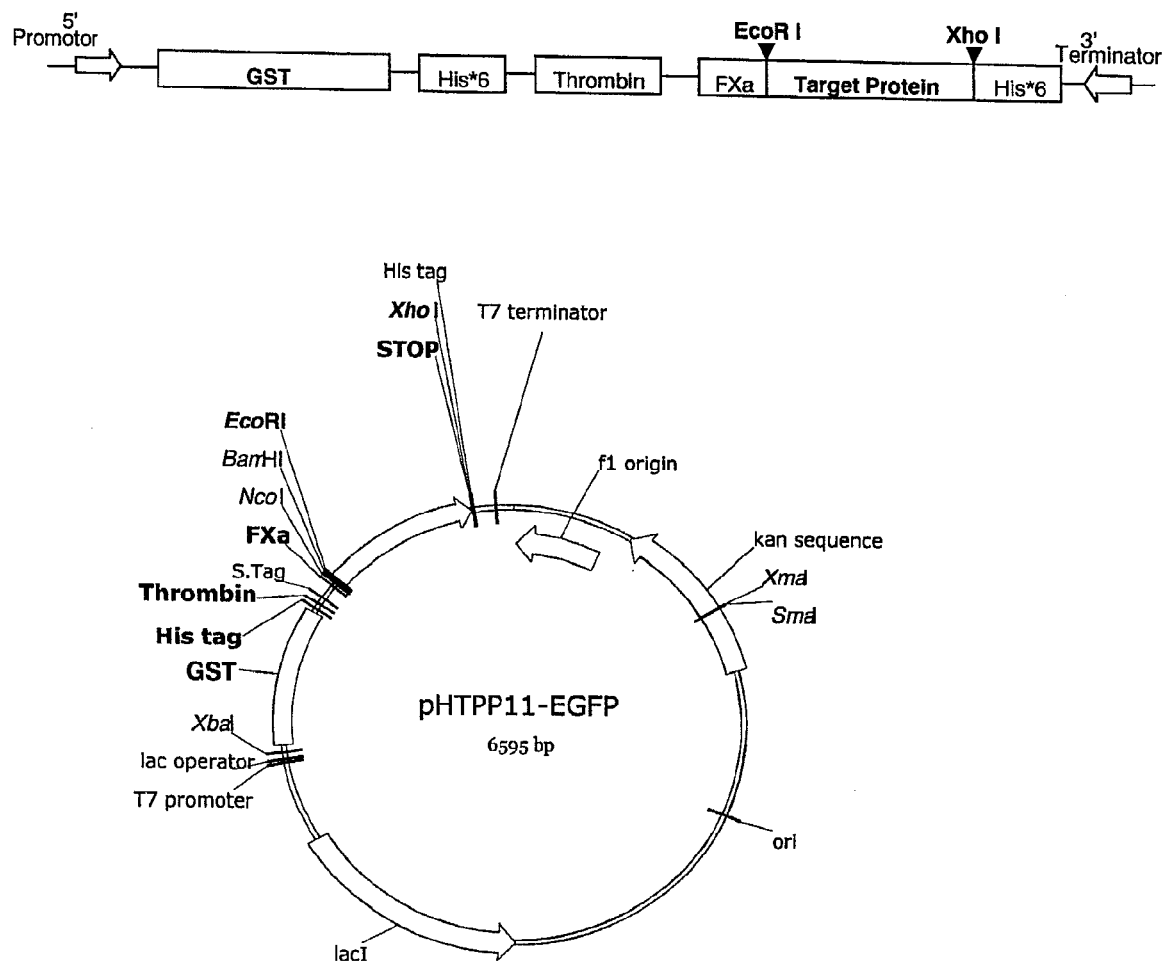

Vector pHTPP11-EGFP (see FIG. 2B) was constructed by ligating the 5'-EcoR I/3'-Xho I-EGFP fragment described above into the EcoR I and Xho I sites of pET-42a(+), which includes a nucleotide sequence encoding a GST fusion tag. The EGFP gene was then removed from vector pHTPP11-EGFP to produce a linear vector pHTPP11.

Figure 2C:
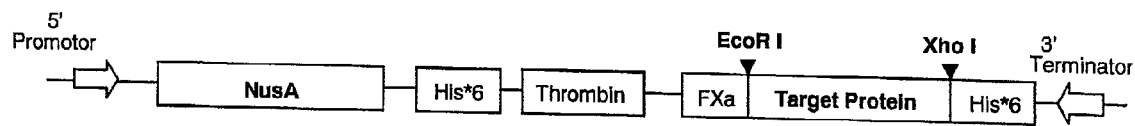
Figure 2C:
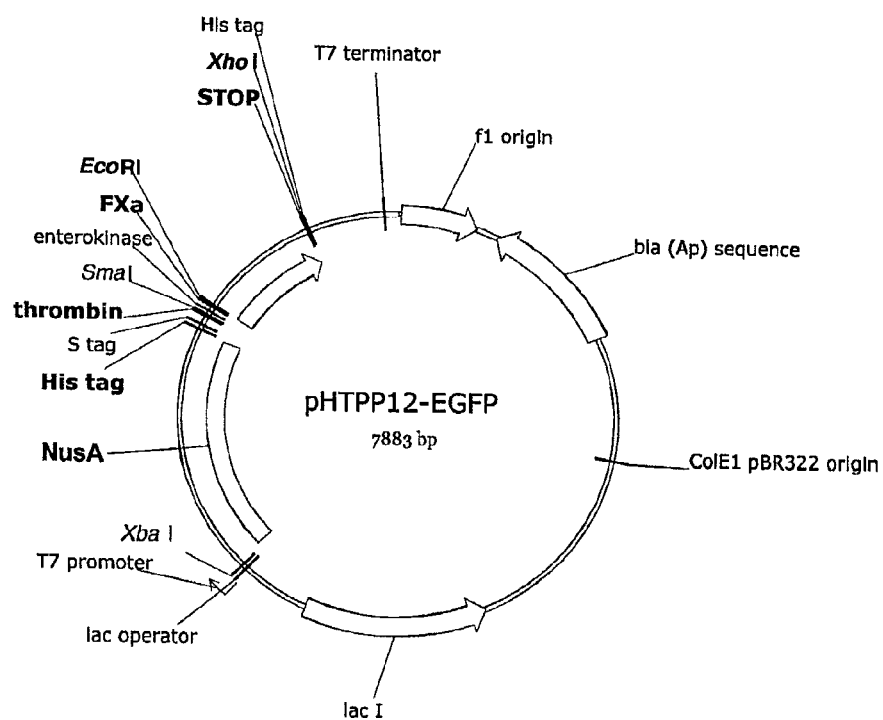

Vector pHTPP12 was prepared following the procedures below. Two pairs of primers 5'-CTAGAAATAATTTTGTT-TAACTTTAAGAAGGA-3' (SEQ ID NO: 10) and 5'-AAATAATTTTGTTTAACTTTAAGAAGAG-3' (SEQ ID NO: 11); and 5'-AATTCCCTTCCCTCGATACGAGCTCC-3' (SEQ ID NO: 12) and 5'-C CCTTCCCTCGATAC-GAGCTCC-3' (SEQ ID NO: 13) were used to amplify the segment between Xba I and EcoR I of pET-43.1a(+). The sticky-end PCR product thus obtained contained a nucleotide sequence that encodes an FXa protease site upstream of the EcoR I site. pET-43.1a(+), digested with the restriction enzymes Xba I and EcoR I, was then ligated with the sticky-end PCR product to form pHTPP12 (NusA tag, 65.7 kDa). An EGFP gene was cloned into this vector via EcoRI/XhoI sites to produce pHTPP12-EGFP (see FIG. 2C).

Figure 2D:
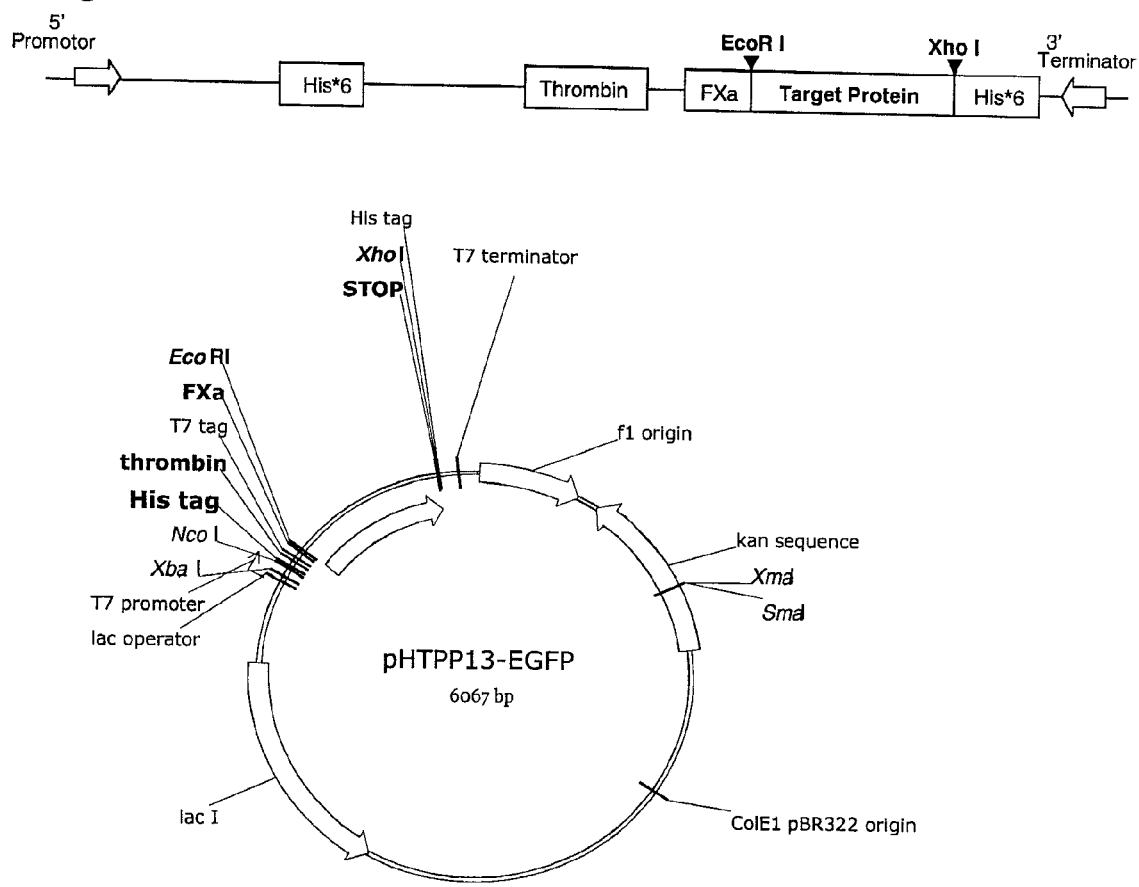
Figure 2E:
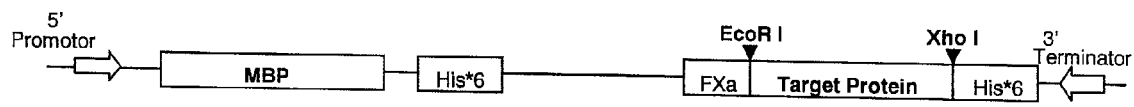
Figure 2E:
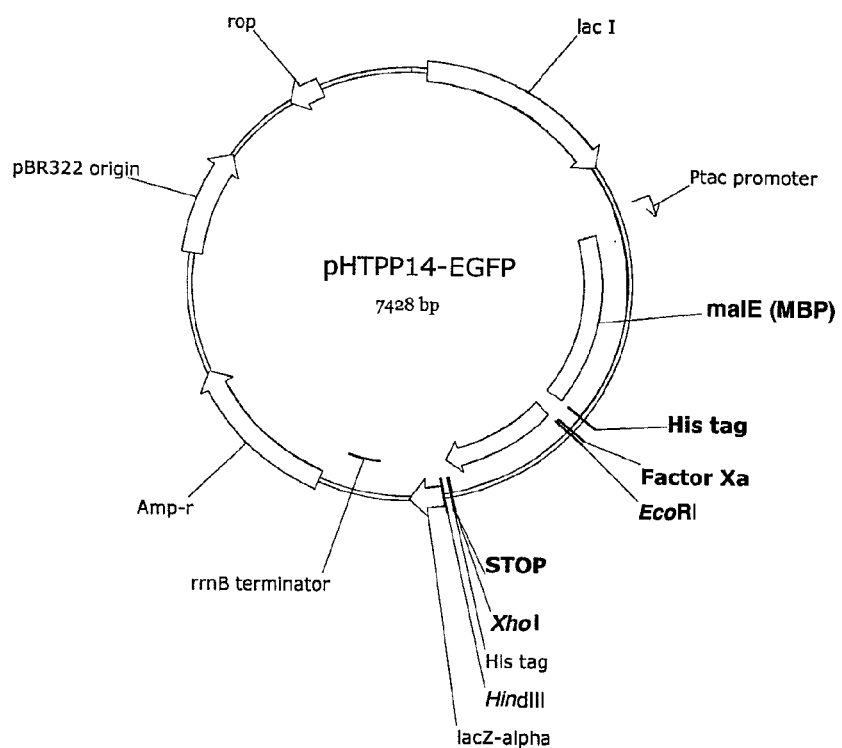
Figure 2F:
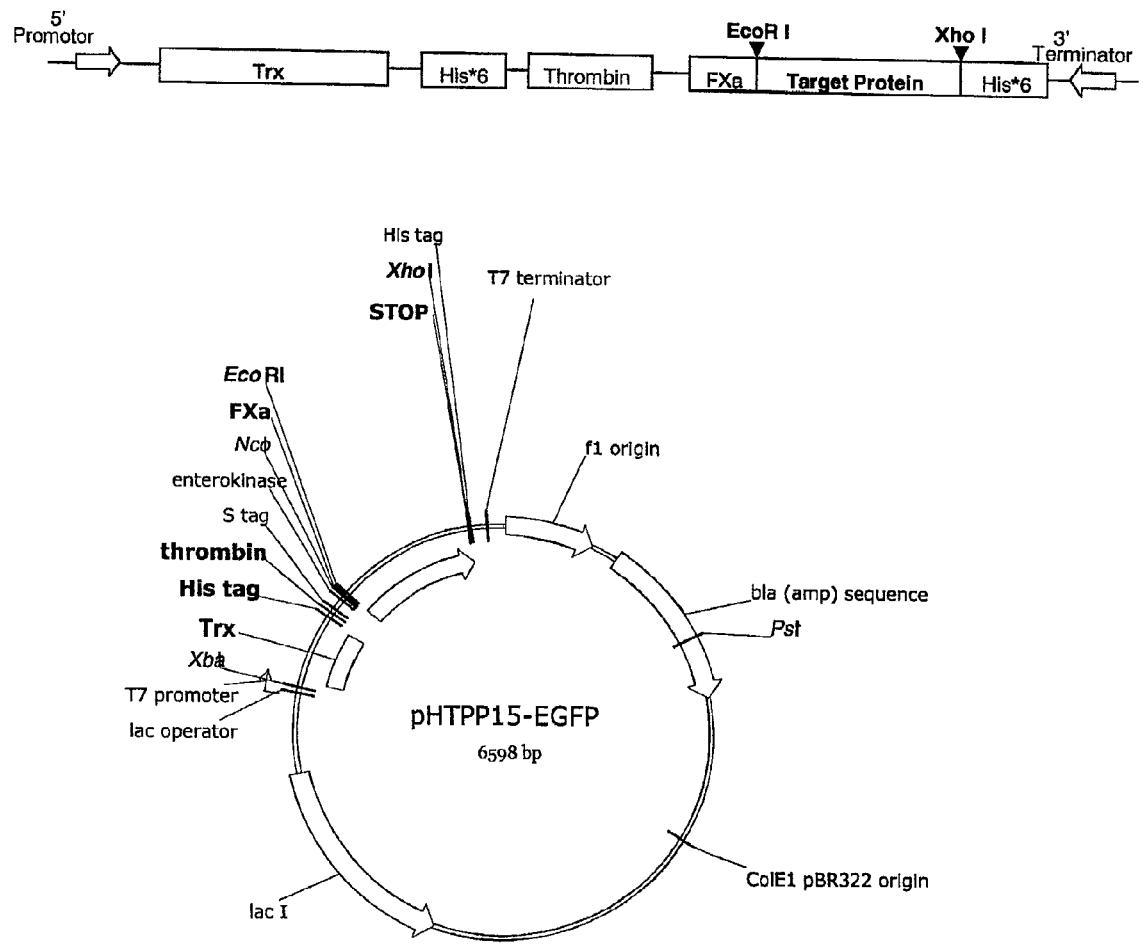
Figure 2G:
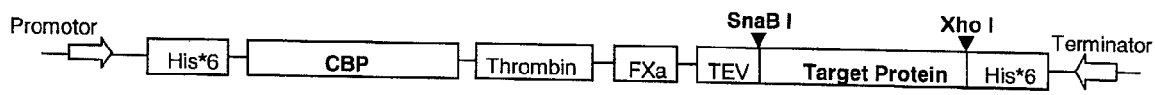
Figure 2G:
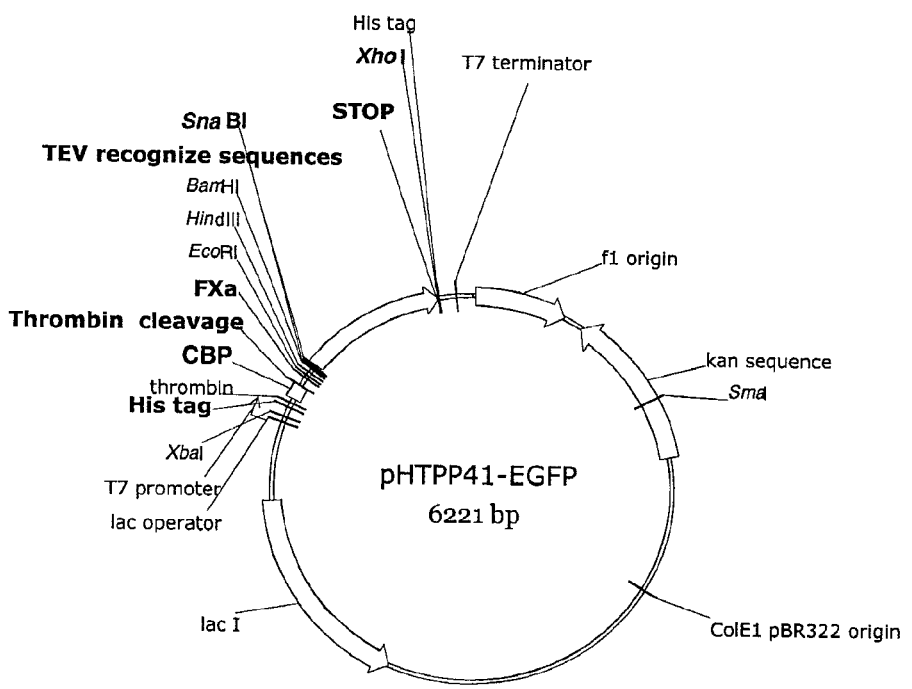
Figure 2H:
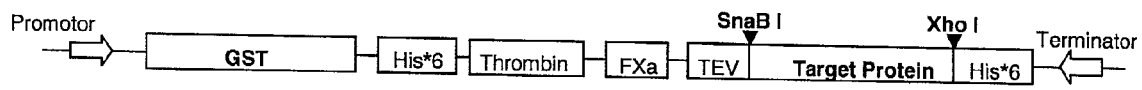
Figure 2H:
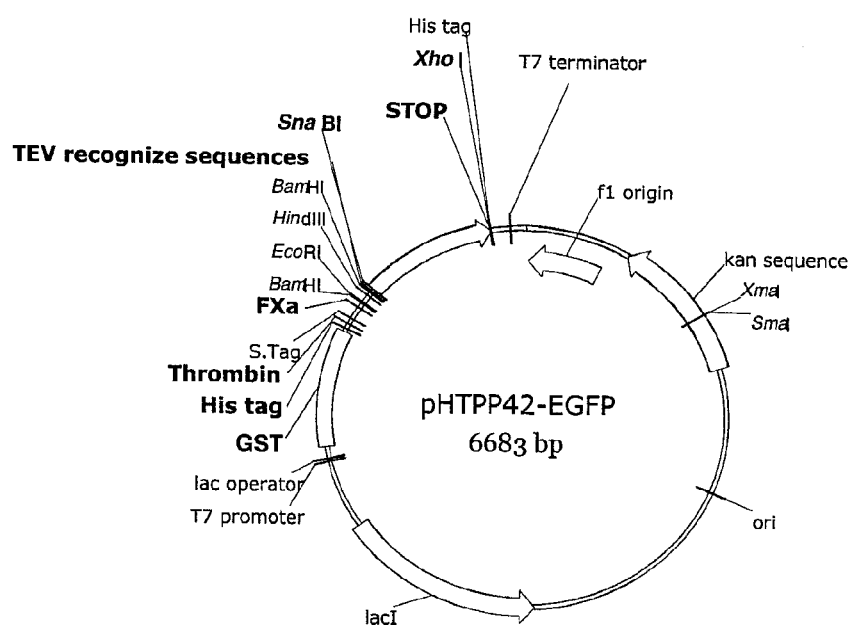
Figure 2I:
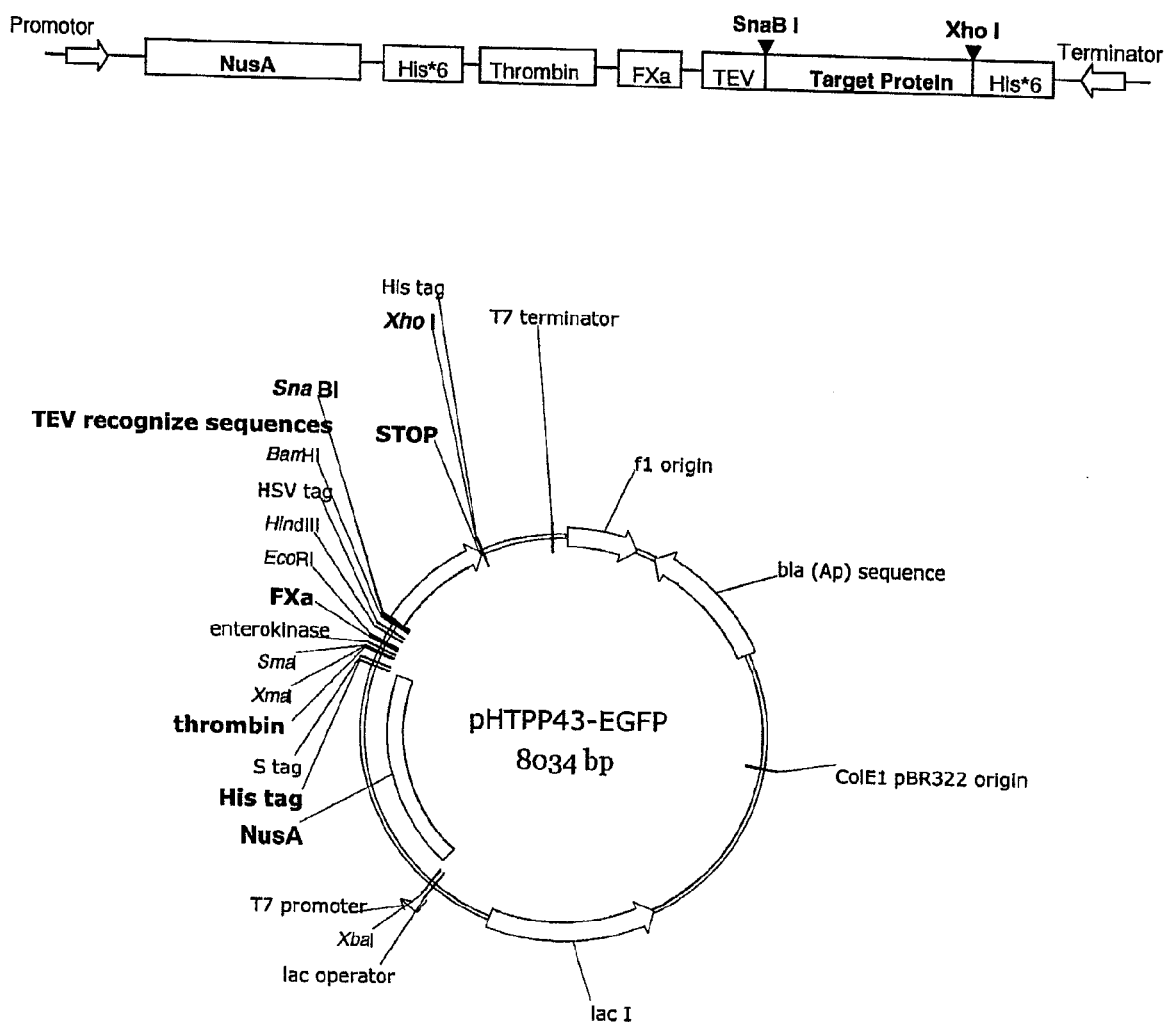
Figure 2J:
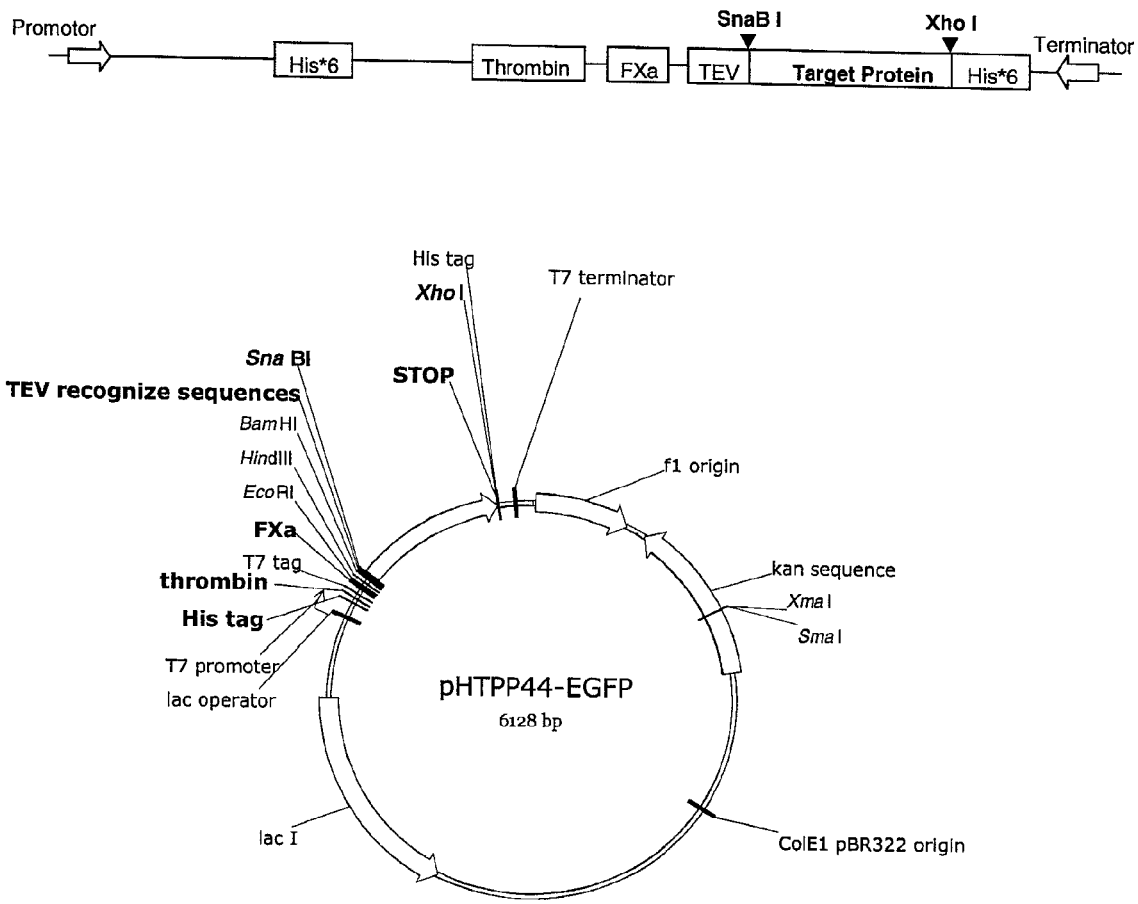
Figure 2K:
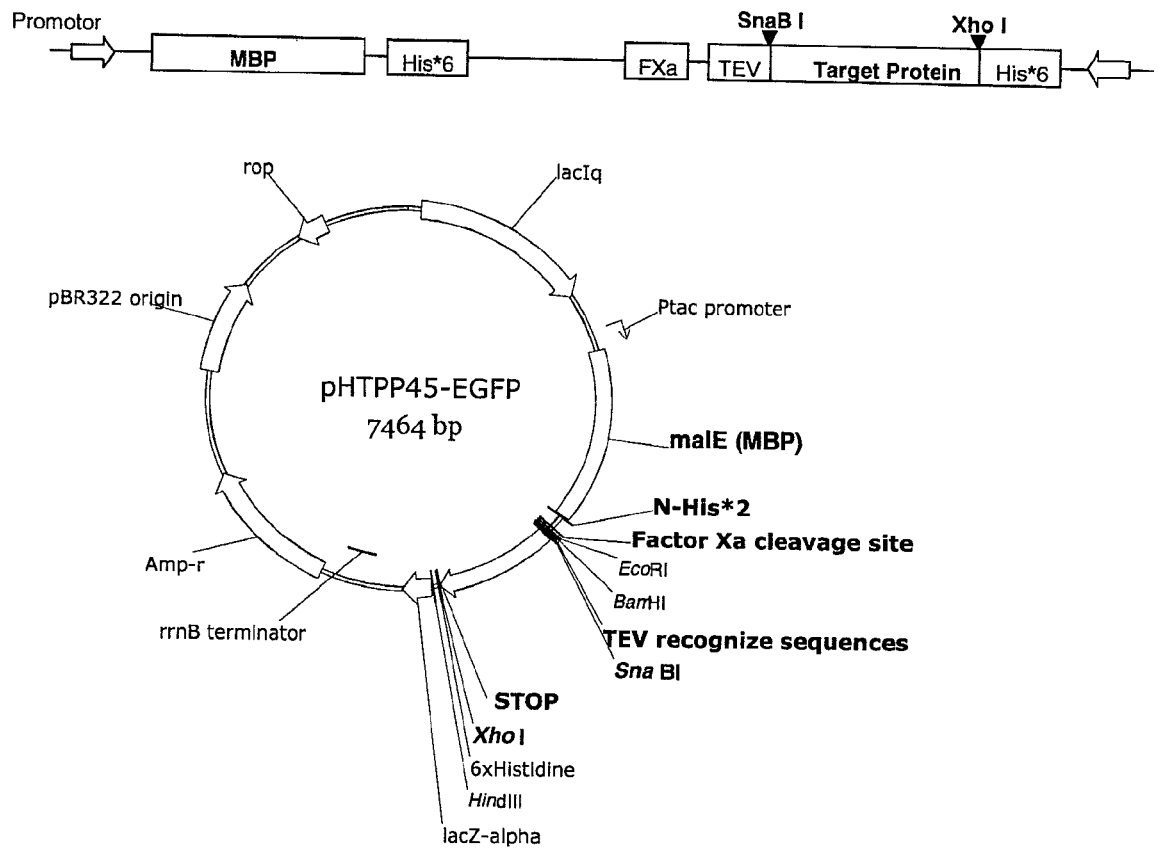

Vector pHTPP13 was generated as follows. Sticky-end PCR was performed to amply the segment between Xba I and EcoR I of commercial vector pET-28a, using the following two pairs of primers 5'-CTAGAAATAATTTTGTTTAACTT-TAAGAAGGA-3' (SEQ ID NO: 10) and 5'-AAATAATTTTGTTTAACTTTAAGAAGAG-3' (SEQ ID NO: 11); and 5'-AATTCCCTTCCCTCGATGCGAC-CCATTT GCTGTCCACC-3' (SEQ ID NO: 14) and 5'-CCCTTCCCTCGATGCGACCCATTTGCTGTCCACC-3' (SEQ ID NO: 15). The sticky-end PCR product thus obtained contains a nucleotide sequence encoding an FXa protease site upstream of the EcoR I site. The PCR product was cloned into the XbaI/EcoRI sites of pET-28a to generated the pHTPP13 vector, which contained the fusion a nucleotide sequence encoding a hexa-His tag (SEQ ID NO: 71) (6.4 kDa) and the EcoR I/Xho I sites for cloning a target gene, e.g., an EGFP gene (see FIG. 2D).

pHTPP14 vector was prepared by inserting a fragment encoding a hexa-His tag (SEQ ID NO: 71) and including an Sac I site into pMAL-c2X vector, which includes a nucleotide sequence encoding an MBP tag (46.3 kDa). The above-mentioned fragment was produced by annealing the following two oligos 5'-TGCACCACCATCACCATCACAGCT-3' (SEQ ID NO: 16) and 5'-GTGATGGTGAT GGTGGTG-CAAGCT-3' (SEQ ID NO: 17). It was then ligated with the Sac I-treated pMAL-c2X vector to form pHTPP14. An EGFP gene was cloned via the EcoR I and Xho I sites of this vector to produce pHTPP14-EGFP (see FIG. 2E).

pHTPP15 was generated from pET-32a(+) as follows. Two pairs of PCR primers 5'-CTAGAAATAATTTTGTT-TAACTTTAAGAAGGA-3' (SEQ ID NO: 10) and 5'-AAATAATTTTGTTTAACTTTAAGAAGAG-3' (SEQ ID NO: 11); and 5'-AATTCCCTTCCCTCGATGATATCAGC-3' (SEQ ID NO: 18) and 5'-CCCTT CCCTCGATGATAT-CAGC-3' (SEQ ID NO: 19) were used to amplify the segment between XbaI and EcoRI of pET-32(a). The resultant sticky-end PCT product contained a nucleotide sequence encoding an FXa protease site upstream of the EcoR I restriction enzyme site. It was cloned into the XbaI/EcoRI sites of pET-32a(+) to generate pHTPP15, which contains a nucleotide sequence encoding a Trx fusion tag (20 kDa), and the EcoRI/XhoI sites for cloning a target gene, e.g., an EGFP gene (see FIG. 2F).

pHTPP41, pHTPP42, pHTPP43, pHTPP44, pHTPP45, and pHTPP46 were generated by inserting a double-strand oligonucleotide into the Xho I site of pHTPP10, pHTPP11, pHTPP12, pHTPP13, pHTPP14, and pHTPP15, respectively. The oligonucleotide, encoding a TEV protease recognition site and including an SnaB I site, was prepared by annealing two primers 5'-TCGAAGGATCCGGTGGTGAGAACCTG-TACGTACAGGGAGGTGGTC-3' (SEQ ID NO: 20) and 5'-TCGAGACCACCTCCCTGTACGTACAGGT-TCTCACCACC GGATCCT-3' (SEQ ID NO: 21).

The EGFP gene mentioned above was cloned into these vectors via the SnaB I site and an Xho I site to form pHTPP41-EGFP, pHTPP42-EGFP, pHTPP43-EGFP, pHTPP44-EGFP, pHTPP45-EGFP, and pHTPP46-EGFP. See FIGS. 2G-2L. An EGFP-tag fusion protein expressed from any of these vectors, when cleaved by the TEV protease, yielded an EGFP protein having the exact amino acid sequence encoded by the EGFP gene. See FIG. 1, top panel.

EXAMPLE 2

Production of Tag-Cleavable Fusion Proteins in *E. Coli* Cells

Expression vectors pHTPP10-EGFP, pHTPP11-EGFP, pHTPP12-EGFP, pHTPP13-EGFP, pHTPP14-EGFP, pHTPP15-EGFP, and pHTPP45-EGFP were transformed into *E. coli* BL21 (DE3) cells for protein expression. In the presence of Ampicillin, the transformed cells were grown in the Luria-Bertani (LB) medium until the bacterial cultures reached an $OD_{600}$ value of about 0.6. The cells were then induced with 0.1 mM isopropylthio-β-D-galactoside (IPTG) and cultured at 20° C. for 24 h. The cells were harvested by centrifugation at 10,000 g and cell pellets were resuspended in 100 µL FIT buffer (20 mM Tris-HCl, 150 mM NaCl, 50 mM sucrose, 0.5 mM EGTA, 0.1 mM TPCK, and 10% glycerol, pH 8.0) and disrupted using a sonicator (Sonicatori; dr. hielscher, UP-100H). The sonicator generated ultrasound energy at 30 kHz from 0-100 watts with a pulse rate of up to 30 sec in 5-sec intervals. The total cell lysates thus obtained were first subjected to centrifugation at 100,000 g for 40 min, and the supernants, containing soluble proteins, were loaded onto columns packed with 100 µL Ni-NTA resin (Novagen, Germany). The columns were then washed with 500 µl HT buffer containing 0, and then 30 mM imidazole (pH 8.0) and eluted with 50 µL HT buffer each containing 100, 250 and 500 mM imidazole (pH 8.0). The fractions containing tag-EGFP fusion proteins were pooled and dialyzed against a dialysis buffer to remove imidazole. The fusion proteins were treated with FXa to remove the tag.

Purified fusion proteins, before or after protease treatment, were subjected to SDS-PAGE and then stained with Coomassie blue. A protein band at ~30 kD was observed on SDS-PAGE after a fusion protein was digested with either FXa or the TEV protease, indicating that FXa cleavage released the EGFP proteins (30 kD).

EXAMPLE 3

Figure 3A:
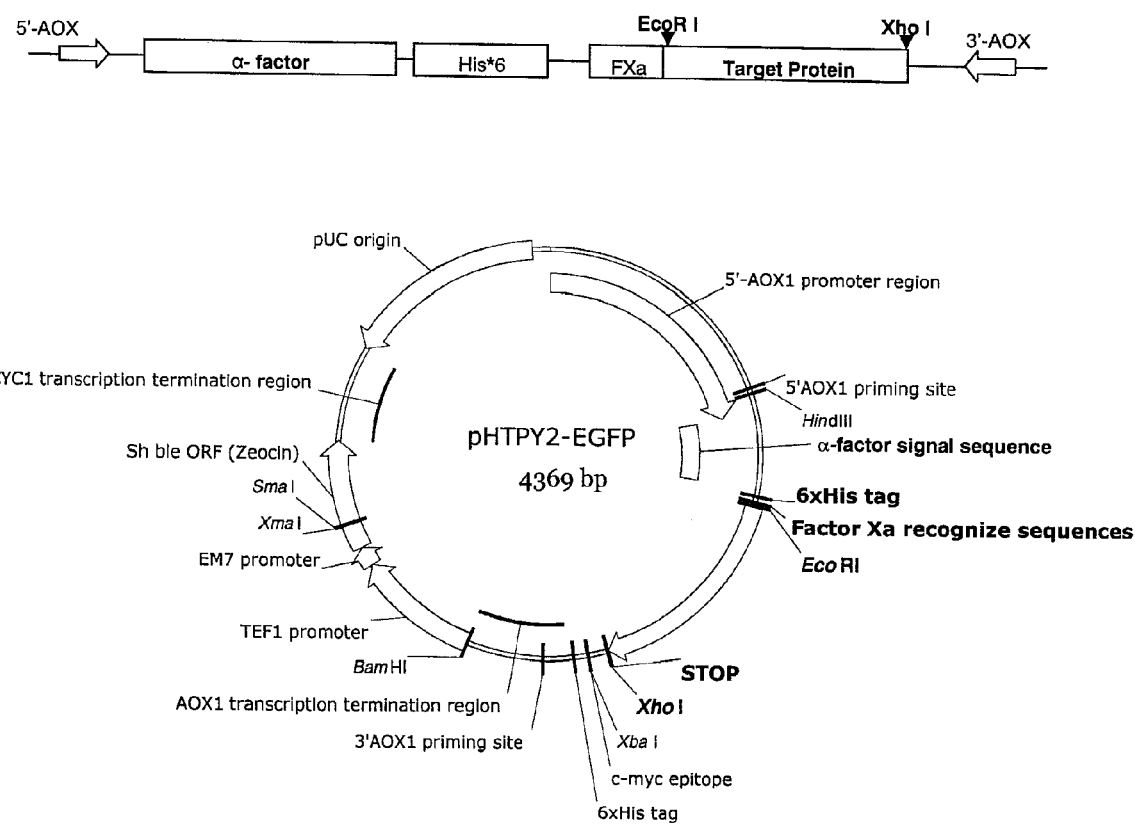
FIG. 3 is a set of maps of expression vectors for protein expression in yeast cells. A: vector pHTPY2 with EGFP gene cloned therein; B: vector pHTPY4 with EGFP gene cloned therein (6× His tags disclosed as SEQ ID NO: 71).
Figure 3B:
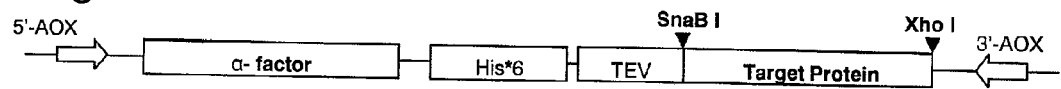
Figure 3B:
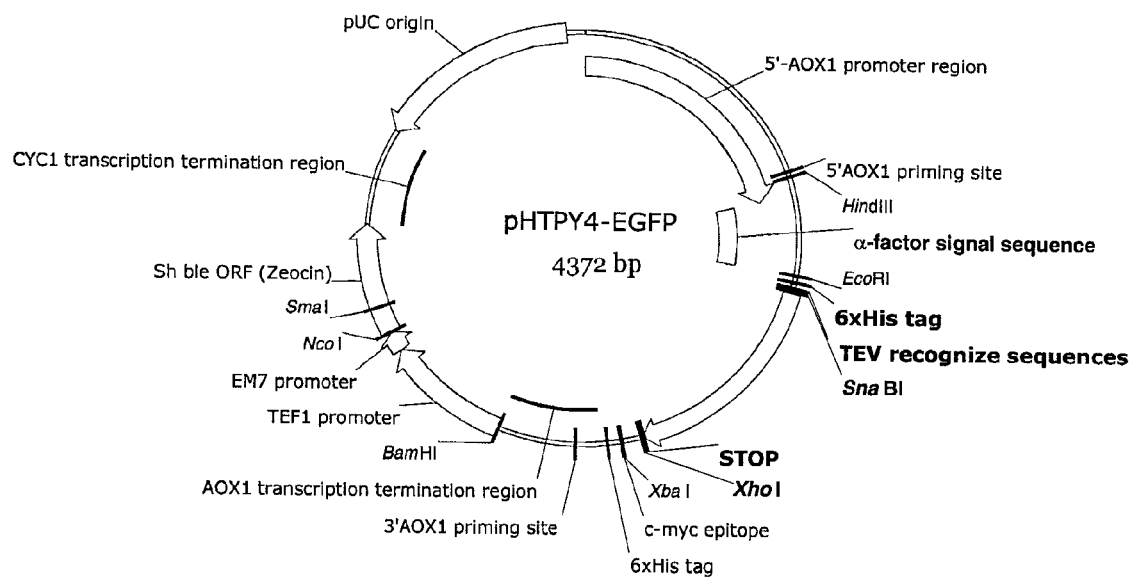

Construction of Expression Vectors for Producing Tag-Cleavable Fusion Proteins in Yeast Cells A yeast expression vector pHTPY2 was constructed by modifying a fusion protein expression vector pPICZαA (without His-tag and FXa protease sites) purchased from Invitrogen. Two oligonucleotides, 5'-TCGAAAAAA-GAGAGGCTGAAGCTGAATTCTGCAGCTCGACGT GGC CCAGCCGGCCGTCTCGGATCGGTACG-3' (SEQ ID NO: 22) and 5'-TCGACGTAC CGATCCGAGACGGC-CGGCTGGGCCACGCTCGAGCT GCAGAATTCAGCT-TCAGCCTCTCTTTTT-3' (SEQ ID NO: 23), were annealed to form a double-stranded fragment including an EcoR I site and an altered Xho I site (when ligated with an Xho I-digested site, the resultant site cannot be digested by Xho I). The fragment was then phosphorylated and ligated to pPICZαA digested with Xho I. Next, this resultant plasmid was subjected to further modification to insert a His-tag and a nucleotide sequence encoding the FXa recognition site as follows. Two oligos, 5'-AATTGACTAGTGGGGCTAGCCATCAT-CATCATCATCATATCGAGGGAAGGG-3' (SEQ ID NO: 24) and 5'-AATTCCCTTCCCTCGATATGATGATGATGAT GATGGCTAGCCCCACTAGTC-3' (SEQ ID NO: 25) (5'-EcoR I*-Spe I-Nhe I-His-tag-FXa-EcoR I-3') were annealed, phosphorylated, and then ligated to the just-mentioned plasmid, which was digested with EcoR I to form the pHTPY2 vector. The EGFP gene obtained as described above was then cloned into this vector via EcoR I and Xho I to generate pHTPY2-EGFP. See FIG. 3A.

pHTPY2 was digested with Xho I and ligated with a DNA fragment formed by annealing and then phosphorylating the oligonucleotides 5'-TCGAAAAAAGAGAGGCTGAAGCT-GAA TTCTACGTAGGGCTCGAGCGTGGC CCAGCCG-GCCGTCTCGGATCGGTACG-3' (SEQ ID NO: 26) and 5'-TCGACGTAC CGATCCGAGACGGCCGGCTGGGC-CACGCTCGAGCCCTACGTAGAATTCAGCT TCAGC-CTCTCTTTTT-3' (SEQ ID NO: 27) (5'-Xho I*-EcoR I-SnaB I-Xho I*-3') to produce vector pHTPY3. This vector was digested with Spe I/SnaB I and ligated with a DNA fragment formed by annealing and then phosphorylating oligos 5'-AC-TAGTGGGGCTAGCCATCATCATCATCATCATGAGA ACCTGTAC-3' (SEQ ID NO: 28) and 5'-GTACAGGTTCT-CATGATGATGATGATGATGGCTAGC CCCACTAGT-3' (SEQ ID NO: 29) to form vector pHTPY4. This DNA fragment encodes the TEV protease site and a His-tag, and includes an SnaB I site. The EGFP gene was then cloned into this vector to produce pHTPY4-EGFP. See FIG. 3B.

EXAMPLE 4

Production of EGFP-Tag Fusion Protein in Yeast Cells

Vectors pHTPY2 and pHTPY4 were transformed into yeast Pichia via electroporesis at 2,000 V for 5 msec with 5-sec pulse interval using exponential decay mode of electroporator (BioRad, USA). The transformed yeast cells were grown and the colonies showing a high resistant level to Zeocin (300 mg/L) were selected. A selected single colony was inoculated in 50 ml of Buffered Glycerol-complex Medium (BMGY) in a 500 ml baffled flask. The yeast cells were grown at 30° C. in a shaking incubator (300 rpm) until the culture reached an $OD_{600}$=2-6 (after approximately 16-18 h). The cells were harvested by centrifugation at 3,000 g for 5 mins at room temperature. A cell pellet thus formed was resuspended in ⅕ to 1/10 (5-10 mL) of the original culture volume of Buffered Methanol-complex Medium (BMMY) (approximately 100-200 ml). Both BMGY and BMMY contained 1% yeast extract, 2% peptone, 100 mM potassium phosphate, pH 6.0, 1.34% YNB (13.4 g of yeast nitrogen base with ammonium sulfate and without amino acids in 1000 ml of water), 4×10-5% biotin, and 1% glycerol or 0.5% methanol. 100% methanol was added to the culture to reach a final concentration of 0.5% every 24 hours until day 6.

At day 6 the yeast cells were harvested by centrifugation at 3,000 g and the supernant thus formed was collected. Fusion proteins expressed from the above-mentioned two vectors, containing α-factor, were secreted to the medium, which was collected for protein purification by affinity column chromatography. The purified fusion proteins were concentrated and dialyzed against a buffer containing 20 mM Tris-HCl, pH 8, 200 mM NaCl, and 2 mM $CaCl_2$. The α-factor tag was removed by F-actor Xa (Novagen, Germany).

If a fusion protein is located in cytoplasma or nuclei, a glass-bead apparatus can be used to break the yeast cell membranes. The resultant lysate was centrifuged at 9,000 g, and the supernant thus formed was collected and subjected to further protein purification.

Purified fusion proteins, before or after protease treatment, were subjected to SDS-PAGE and then stained with Coomassie blue. A protein band at ~30 kD was observed on SDS-PAGE after a fusion protein was digested with either FXa or the TEV protease, indicating that protease cleavage released the EGFP proteins (30 kD).

EXAMPLE 5

Figure 4A:
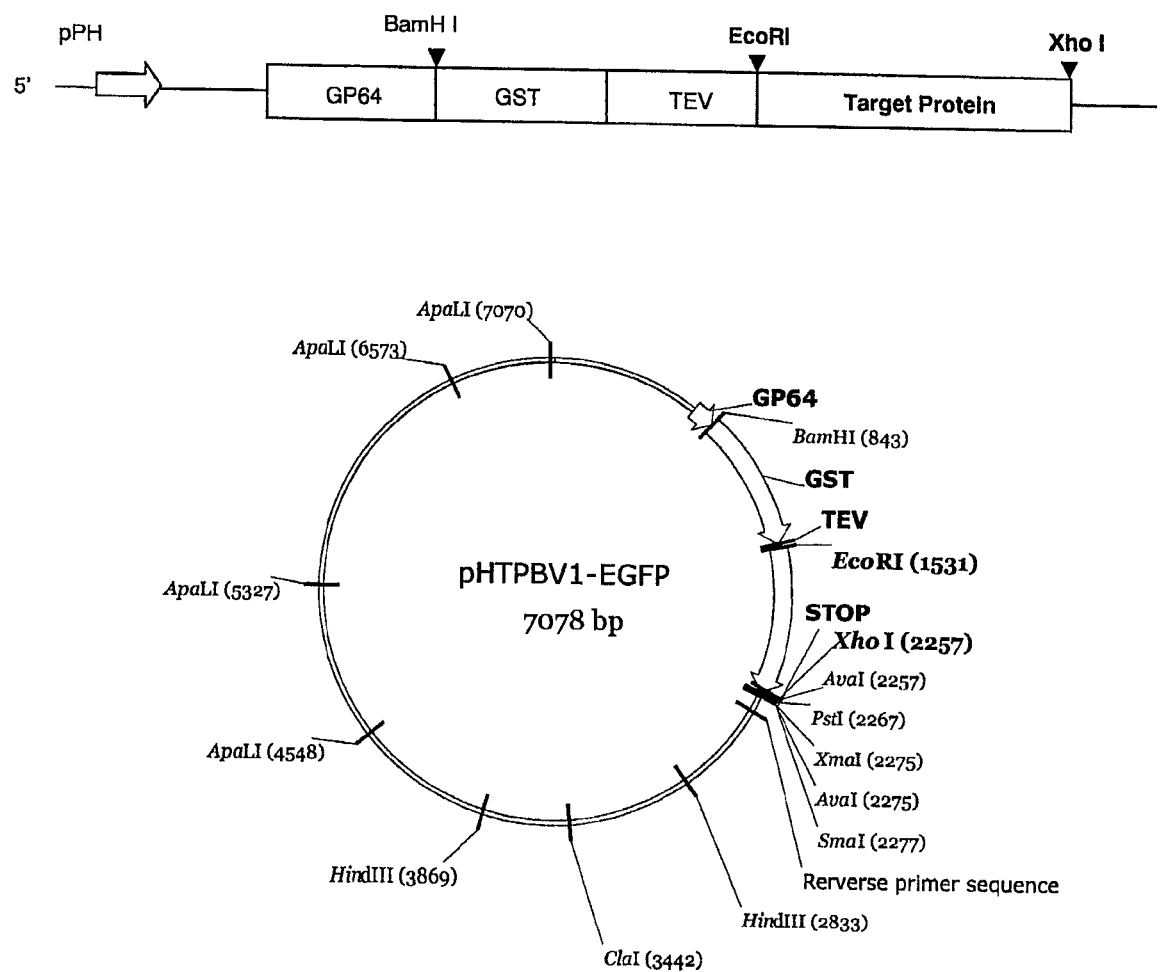
FIG. 4 is a set of maps of expression vectors for protein expression in insect cells. A: vector pHTPBV1 with EGFP gene cloned therein; B: vector pHTPBV2 with EGFP gene cloned therein; C: vector pHTPBV3 with EGFP gene cloned therein; D: vector pHTPBV4 with EGFP gene cloned therein; E: vector pHTPBV5 with EGFP gene cloned therein; and F: vector pHTPBV6 with EGFP gene cloned therein.
Figure 4B:
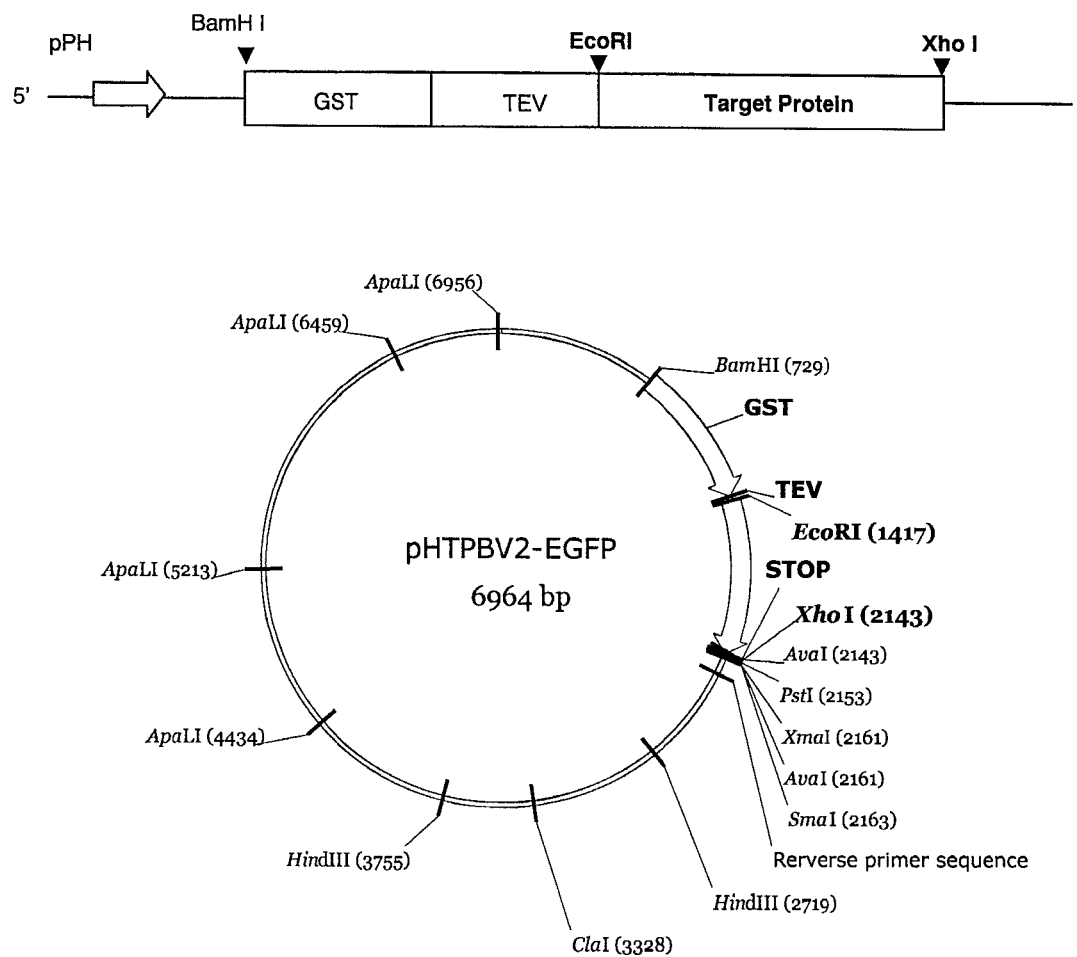
Figure 4C:
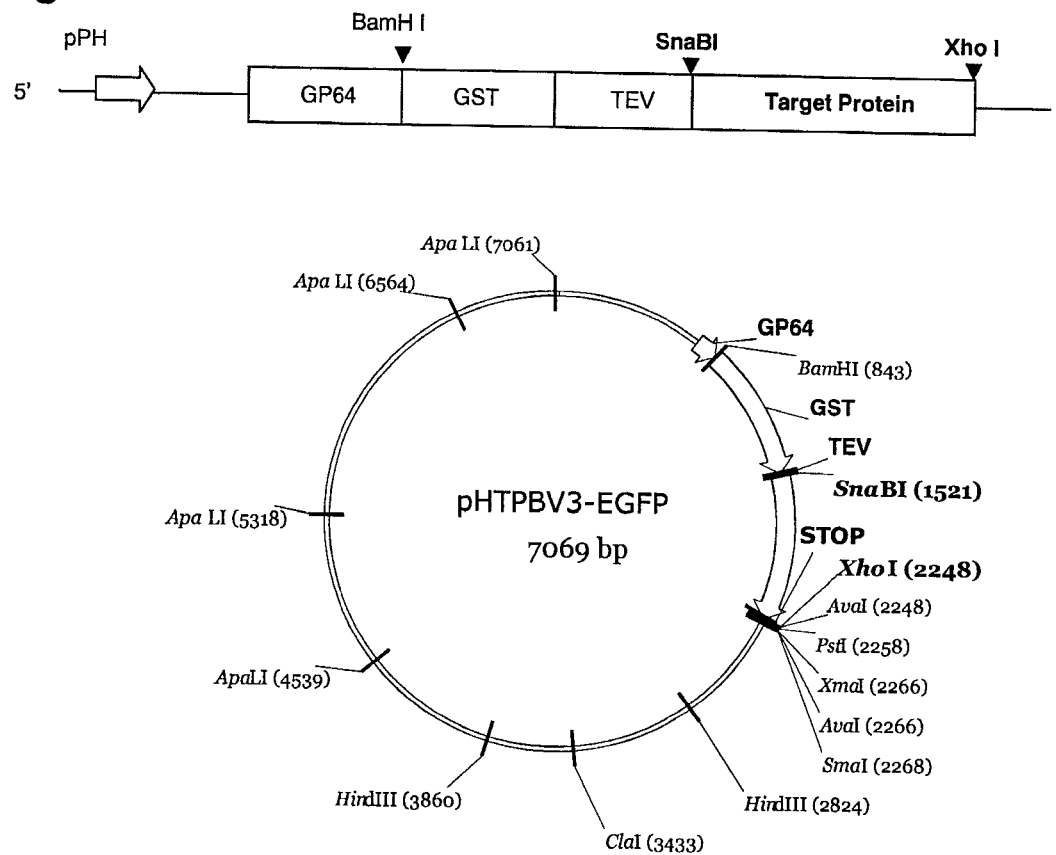

Construction of Expression Vectors for Producing Tag-Cleavable Fusion Proteins in Baculovirus Expression System Three pPH promoter-derived expression vectors (pHT-PBV1-3, see FIG. 4A-C) were constructed following the procedures below. Sticky-end PCR was performed to produce a 5'-BamH I-GST-TEV-EcoR 1-3' fragment with two pairs of primers 5'-GATCCGATGTCCCCTATACTAGGTTAT-TGGAAA-3' (SEQ ID NO: 30) and 5'-CACCCTGAAAATA-CAGGTTCTCATCCGATTTTGGAGGATGGTC-3' (SEQ ID NO: 31); and 5'-CGATGTCCCCTATACTAGGTTATTG-GAAA-3' (SEQ ID NO: 32) and 5'-AA TTCACCCT-GAAAATACAGGTTCTCATCCGATTTTGGAGGAT GGTC-3' (SEQ ID NO: 33), using pHTPP11 as a template. The sticky-end fragment thus obtained was ligated to pAcSec 1 vector (Orgiben, San Diego, Calif.) digested BamH I and EcoR I to produce pHTPBV1 encoding a GP64 secretary signal peptide, a GST tag and a TEV cleavage site. This vector can be used with Sapphire™ baculovirus DNA (Orbigen) to produce recombinant virus in insect cells.

pHTPBV2 vector, lacking the sequence encoding the GP64 signal peptide, was made as follows. Two primers 5'-GCCGGCATAGTACGCAGCTTCTTC-3' (SEQ ID NO: 34), and 5'-TTCTAGAAGGTACCCGGGATCCGCA-GATCCGCGCCCGA TGGTGGGACG-3' (SEQ ID NO: 35)

were used to amplify the region right upstream of the sequence encoding the GP64 signal peptide from pAcSec1, resulting in a fragment containing a 5'-NgoM IV site. Another two primers 5'-GCGGATCCCGGGTA CCTTCTAGAA-3' (SEQ ID NO: 36), and 5'-ATCGATGTCTGAATTGCCGC-CCGC-3' (SEQ ID NO: 37) were used to produce a second fragment using pAcSec1 vector as the template. This fragment contains a 3'-Cla I site. The first and second fragments were denatured and then annealed, phosphorylated, and ligated with a NgoM IV/Cla I-digested pAcSec1 to produce vector pHTPBV2.

Next, two pairs of primers 5'-GATCCGATGTC-CCCTATACTAGGTTATTGGAAA-3' (SEQ ID NO: 38) and 5'-TGCAGCTCGAGGAATTCTCCCTGTACGTACAG GTTCTCATCCGATTTTGGAGG ATGGTC-3' (SEQ ID NO: 39); and 5'-CGATGTCCCCTATACTAGGTTATT GGAAA-3'(SEQ ID NO: 40) and 5'-GCTCGAGGAAT-TCTCCCTGTAC GTACAGGTTCTCATCCGATTTTG-GAGGATGGTC-3' (SEQ ID NO: 41) were used to generate a sticky-end PCR product, 5'-BamH I-GST-TEV-SnaB I-Xho I-Pst I-3', using pHTPP11 as a template. This PCR fragment was then cloned into the BamH I/Xho I-sites of pHTPBV1 to form pHTPBV3.

Figure 4D:
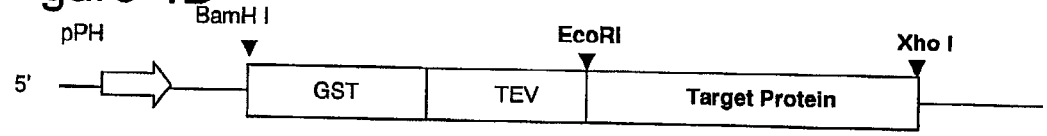
Figure 4D:
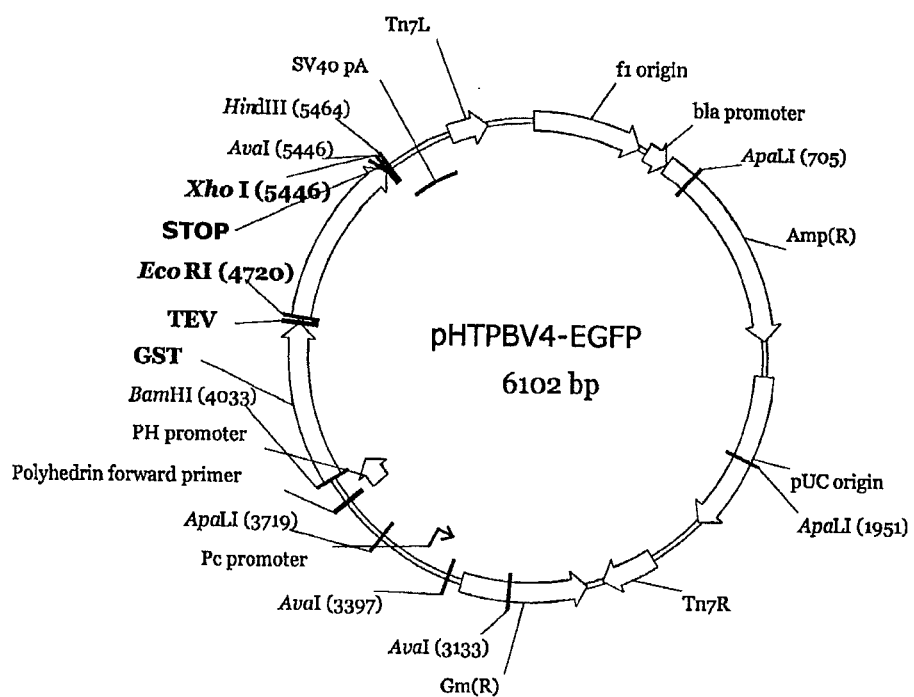

Vectors pHTPBV4-6, compatible with the Bac-to-Bac® baculovirus DNA (Invitrogen) for producing proteins in insect cells, were constructed as follows. A 5'-BamH I-GST-TEV-EcoR 1-3' fragment, encoding a GST tag and the TEV protease recognition site, was prepared by sticky-end PCR using two pairs of primers 5'-GATCCATGTCCCCTATAC-TAGGTTATTGGAAA-3' (SEQ ID NO: 42) and 5'-CAC-CCTGAAAATACAGGTTCTCATC-CGATTTTGGAGGATGGTC-3' (SEQ ID NO: 43); and 5'-CATGTCCCCTATACTAGGTTATTGG AAA-3' (SEQ ID NO: 44) and 5'-AATTCACCCTGAAAATACAGGTTCT-CATCCGATTTTGGAGGATGGTC-3' (SEQ ID NO: 45), and pFastBac™ as a template. This fragment was then cloned into pFastBac™ via its BamH I and EcoR I cloning sites to produce vector pHTPBV4. The EGFP gene was cloned into this vector via EcoR I and Xho I sites to generate pHTPBV4-EGFP (see FIG. 4D).

Figure 4E:
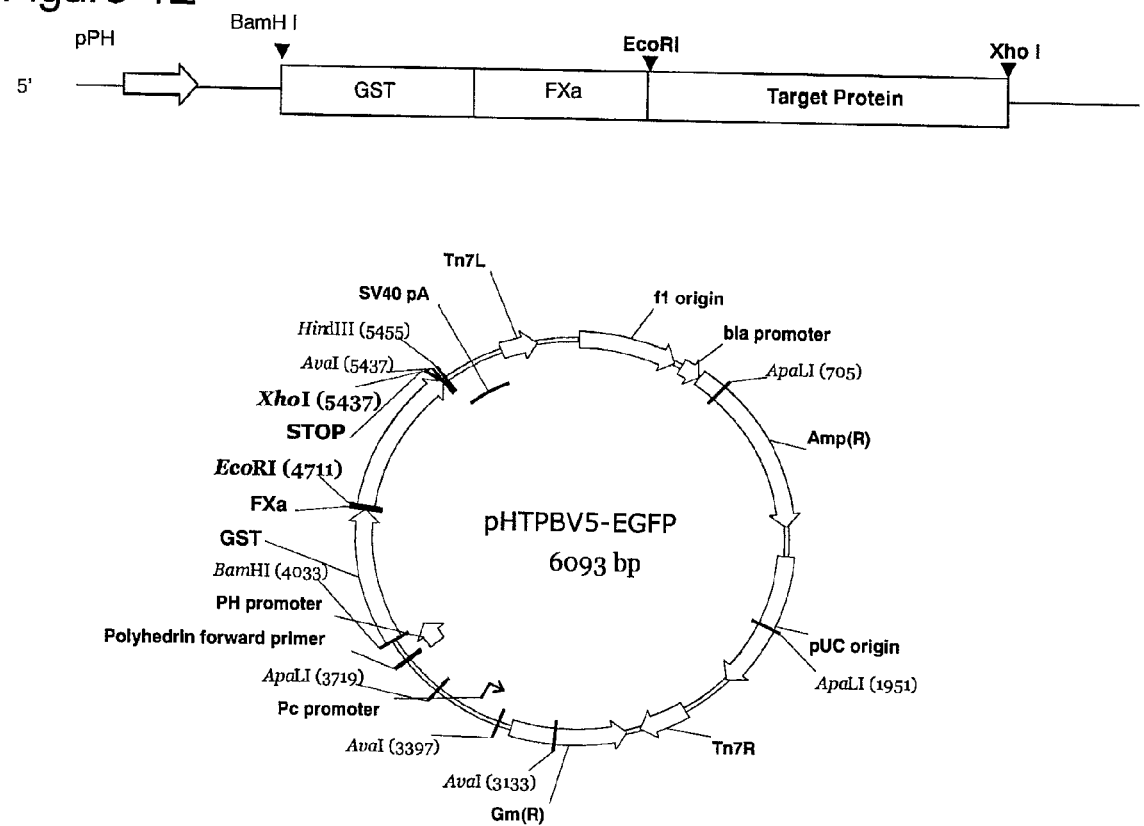

Two pairs of primers, 5'-GATCCATGTCCCCTATAC-TAGGTTATTGGAAA-3' (SEQ ID NO: 42) and 5'-CCCT-TCCCTCGATATCCGATTTTGGAGGATGGTC-3' (SEQ ID NO: 46); and 5'-CATGTCCCCTATACTAGGTTATTG-GAAA-3' (SEQ ID NO: 47) and 5'-AATTCCCTTCCCTC-GATATCCGATTTTGGAGGATGGT C-3' (SEQ ID NO: 48), were used in a sticky-end PCR to produce a fragment 5'-BamH I-GST-FXa-EcoR 1-3', using pHTPP11 as a template. The sticky-end PCR product thus obtained was cloned into pFastBac™ via its BamH I and EcoR I cloning sites to produce vector pHTPBV5. The EGFP gene was cloned into this vector via EcoR I and Xho I sites to generate pHTPBV5-EGFP (see FIG. 4E).

The following two pairs of primers, 5'-GATCCATGTC-CCCTATACTAGG TTATTGGA AA-3' (SEQ ID NO: 42) and 5'-TCGAGGAATTCTCCCTGT ACGTACAGGTTCT-CATCCGATTTTGGAGGAT GGTC-3' (SEQ ID NO: 49); and 5'-CATGTCCCCTATACTAGGTTATTGGAAA-3' (SEQ ID NO: 50), and 5'-GGAATTCTCCCTGTACGTA-CAGGTTCTCATCCGATTTTGGAGGATGGTC-3' (SEQ ID NO: 51), were used to amplify a fragment using pFast-Bac™ as a template. This fragment contains a nucleotide sequence encoding the TEV recognition site and including an SnaB I site. It was cloned into pFastBac™ to form pHTPBV6.

Figure 4F:
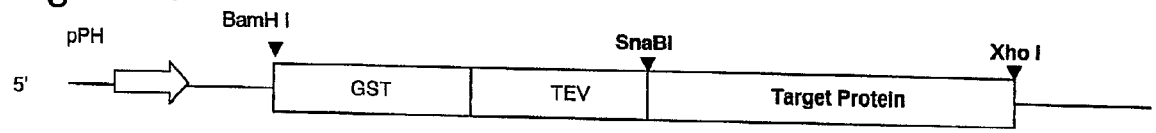
Figure 4F:
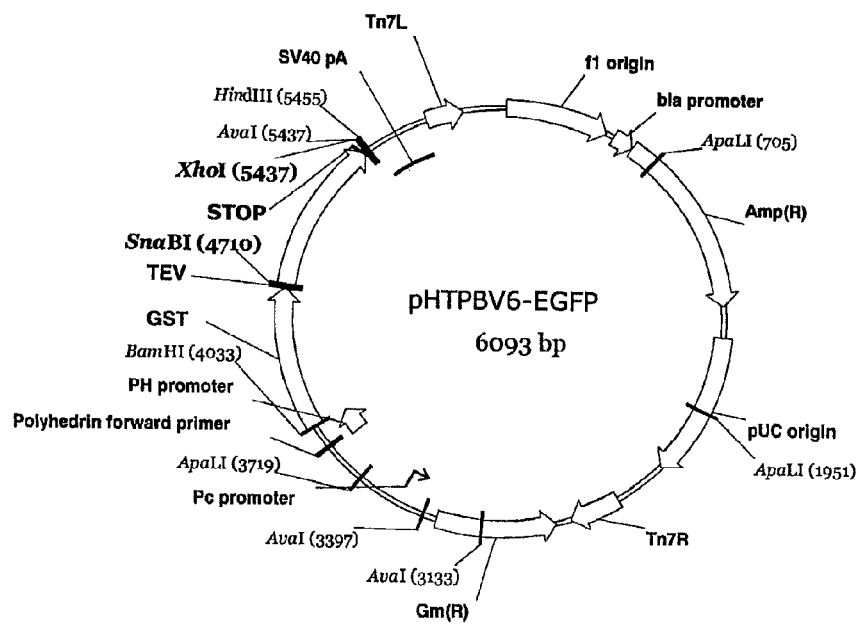

The EGFP gene was then cloned into pHTPBV6 via SnaB I and Xho I to produce pHTPBV6-EGFP (see FIG. 4F).

EXAMPLE 6

Production of Tag-EGFP Fusion Protein in Baculovirus Expression System

High Five cells (Invitrogen B855-02, Carlsbad, Calif.) were cultured (suspended) in a serum-free medium with gentamycin 10 µg/mL (HiClone, Logan, Utah). $1.0 \times 10^7$ cells were infected with pHTPBV1, pHTPBV2, or pHTPBV3, together with Sapphire baculovirus DNA, at a multiplicity of infection (MOI) of 10, using the Sapphire™ transfection kit (Orbigen, no. BVD-10002). A flask containing infected cells was incubated at 28° C. for 3-5 days. The cells were then collected by centrifugation (2,000 g for 5 min), and the supernant thus formed was collect. GST-EGFP fusion proteins contained in the supernant were purified by GST affinity chromatography (Amersham Biosciences, 17-5132-02). Fractions containing the fusion proteins were pooled and dialyzed against a buffer of 10 mM Tris-HCl (pH 8) and 50 mM NaCl.

High Five Cells were also infected with pHTPBV4, pHT-PBV5, or pHTPBV6, together with the Bac-to-Bac baculovirus DNA, using the Bac-to-Bac transfection kit (Invitrogen, no. 10359-016). GST-EGFP fusion proteins were expressed and purified as described above.

The GST-EGFP fusion proteins thus prepared were subjected to protease cleavage with either TEV protease or FXa to yield EGFP protein. The fusion protein expressed from pHTPBV6 releases EGFP proteins having the exact amino acid sequence encoded by the EGFP gene after being cleaved by the TEV protease.

EXAMPLE 7

Figure 5A:
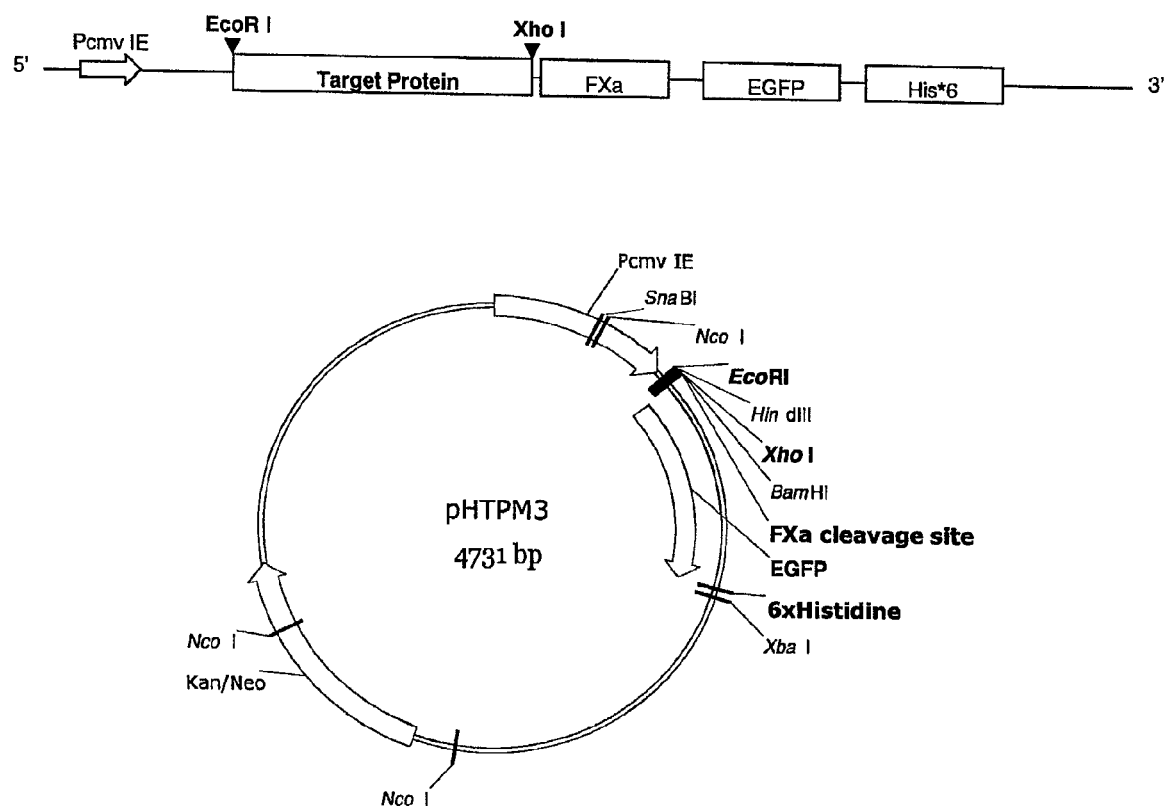
FIG. 5 is a set of maps of expression vectors for protein expression in mammalian cells. A: vector pHTPM3; B: vector pHTPM5; C: vector pHTPM6; and D: vector pHTPM7 (6× His tags disclosed as SEQ ID NO: 71).

Construction of Expression Vectors for Producing Tag-Cleavable Fusion Proteins in Mammalian Cells pHTPM3 vector was constructed by modifying pEGFP-N2 (BD Biosciences Clontech, 6081-1) as follows. An Bgl II-EcoR I-Xho I-FXa-Bam HI fragment was prepared and cloned into pEGFP-N2 via Bgl II/BamH I to produce pHTPM3 (see FIG. 5A). A target gene can be cloned into the EcoR I and Xho I sites of this vector.

Figure 5B:
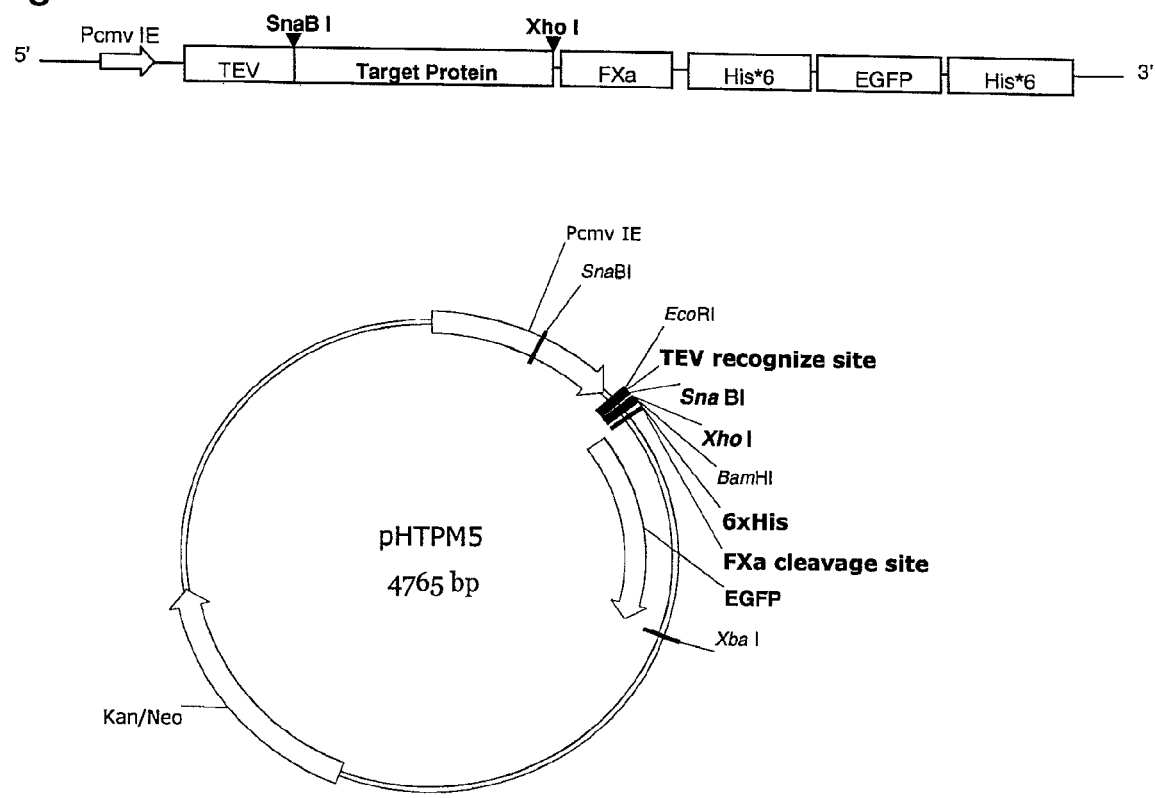

Two primers 5'-GATCTCTGCAGGAATTCGGG-GAGAACCTGTACGTACAGGGAGGTGGTC-3' (5E0 ID NO: 52), and 5'-TCGAGACCACCTCCCTGTACGTACAG-GTTCTCCC CGAATTCCTGCAGA-3'(SEQ ID NO: 53), were used to amplify a fragment 5'-Bgl II-Pst I-EcoR I-TEV-Xho 1-3' using pHTPM3 as a template. In this fragment, a nucleotide sequence encoding the TEV protease recognition site was located upstream of an SnaB I site designed for cloning a target gene. The resultant PCR product was then cloned into the Bgl II/Xho I sites of pHTPM3 to yield the pHTPM3-1. Another two primers 5'-TCGAGGGATC-CGATATCCACCACCACCACCACCA CC-3' (SEQ ID NO: 54), and 5'-GATCGGTGGTGGTGGTGGTGGTG-GATATCGGATCCC-3' (SEQ ID NO: 55) were used to generate a fragment 5'-Xho I-BamH I-EcoR V-His*6-BamH I*-3' (6× His tag disclosed as SEQ ID NO: 71) using pHTPM3-1 as a template. The resultant PCR product was then cloned into Xho I/BamH I-digested pHTPM3-1 to yield vector pHTPM5-EGFP (see FIG. 5B)

Figure 5C:
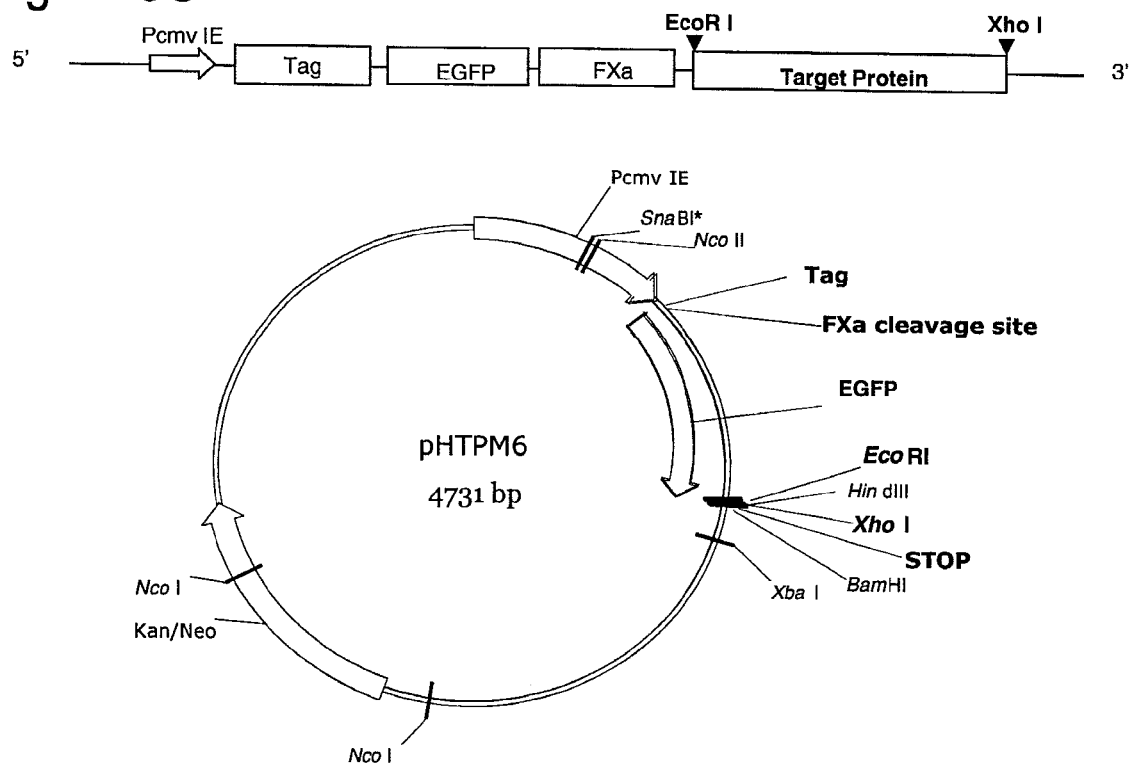
Figure 5D:
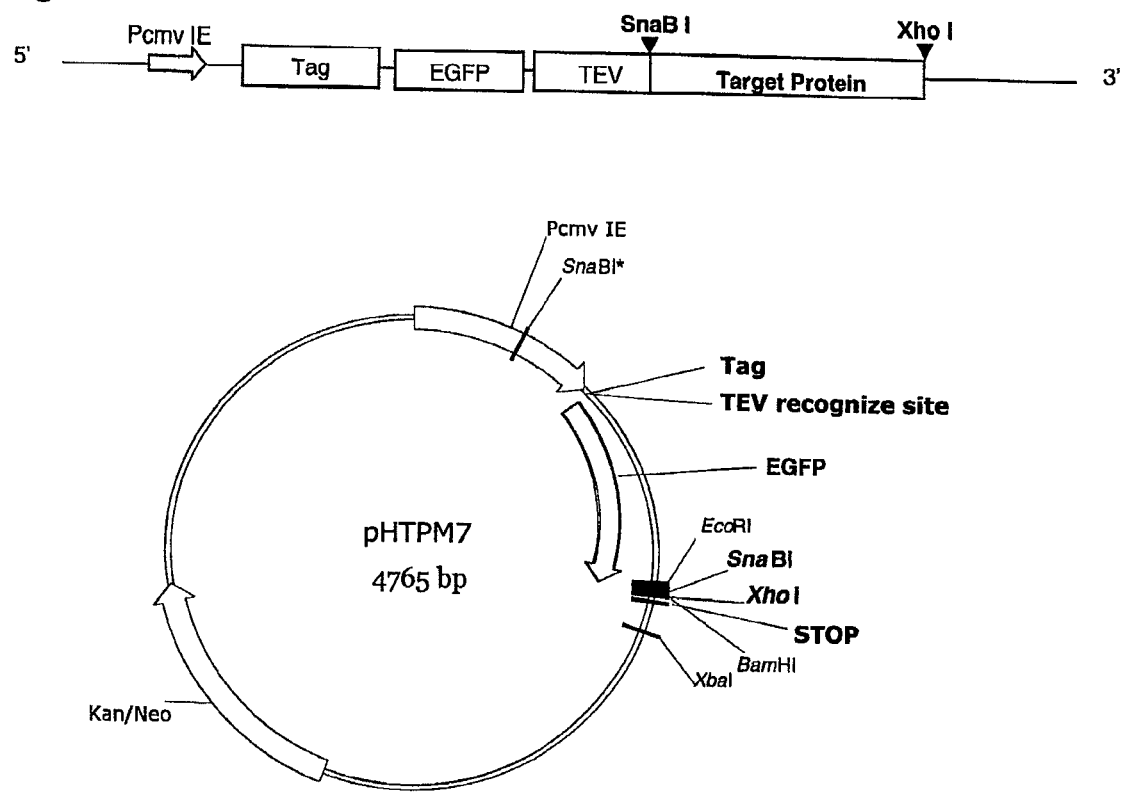

Vector pHTPM6 is constructed by modifying pHTPM3. More specifically, a fragment, containing Bgl II-FXa-EcoR I is prepared and cloned into pHTPM3 via Bgl II/EcoR I sites and the EGFP gene is moved upstream of the FXa site to produce vector pHTPM6. See FIG. 5C. Similarly, vector pHTPM7 is prepared by modifying pHTPM5. More specifically, the TEV-SnaB I-Xho I fragment contained therein is moved to downstream of the EGFP gene to produce pHTPM7. See FIG. 5D.

The above two expression vectors were used to express a target protein fused with EGFP at its C-terminal in mammalian cells. The EGFP tag was used to monitor the expression level of the fusion protein. After purifying the fusion protein via EGFP-affinity chromatography, the EGFP tag was removed by FXa cleavage.

EXAMPLE 8

Figure 6A:
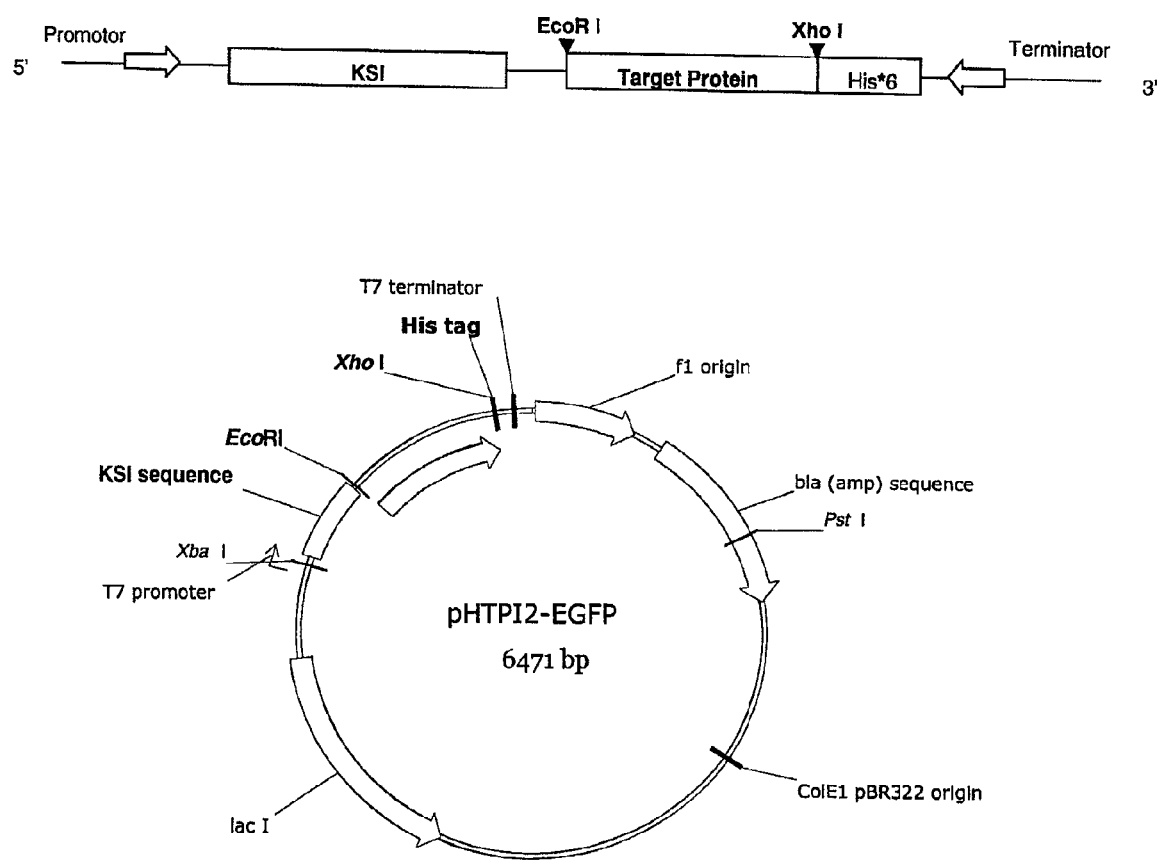
FIG. 6 is a set of maps of expression vectors for protein expression in inclusion bodies. A: vector pHTPI2 with EGFP gene cloned therein; B: vector pHTPI3 with EGFP gene cloned therein (6× His tags disclosed as SEQ ID NO: 71).

Construction of Expression Vectors for Expression of Fusion Proteins E. coli Inclusion Bodies pHTPI2-EGFP vector (see FIG. 6A) was generated by inserting the EGFP gene into vector pET-31b(+) vector. Two pairs of primers 5'-TCGACGAATTC ATGGACAAATT TTGGACTTTC-3' (SEQ ID NO: 56) and 5'-CGAATTCATG GACAAATTTTGGACTTTC-3' (SEQ ID NO: 57); and 5'-TCGAGGTGACTG TGAGCCTCGTG-3' (SEQ ID NO: 58) and 5'-GG TGACTGTGAGCCTCGTG-3' (SEQ ID NO: 59), were used to generate a sticky-end PCR product 5'-Xho I*-EcoR I-EGFP-Xho 1-3'. The PCR product was then cloned into the Xho I site of pET-31b(+). The EGFP gene was then removed from pHTPI2-EGFP by EcoR I and Xho I digestion to produce linear vector pHTPI2.

Figure 6B:
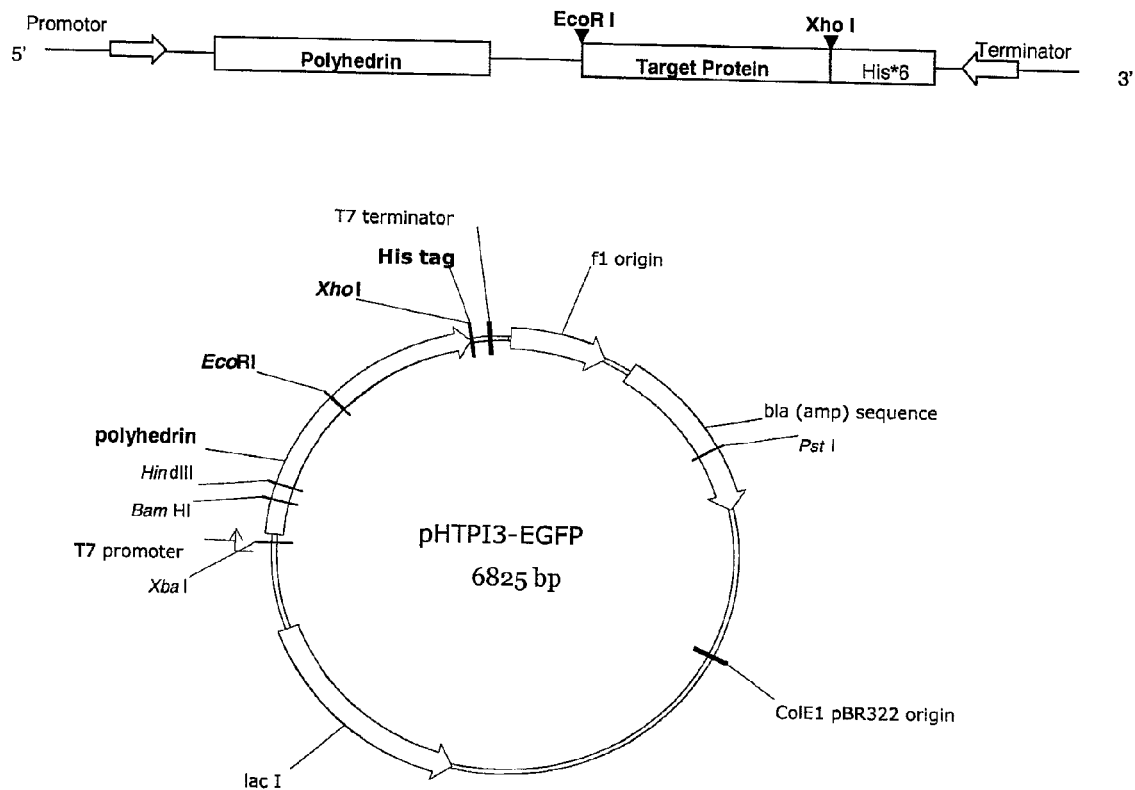

A plasmid including the polyhedrin gene, obtained from Sapphire Baculovirus DNA kit (Orbigen, Autographa californica nuclear polyhydrosis virus), was used as a template for preparing a polyhedron-gene containing DNA fragment. More specifically, the following two pairs of primers used to amplify this fragment: 5'-TATGCCGGATTATTCATACC GTC-3' (SEQ ID NO: 60) and 5'-TGCCGGATTA TTCATACCGTC-3' (SEQ ID NO: 61); and 5'-TCGAGATACGCCG-GACCAG TGAAC-3' (SEQ ID NO: 62) and 5'-GATACGC-CGGACCAGTGAAC-3' (SEQ ID NO: 63). A sticky-end 5'-Nde I-polyhedrin-Xho 1-3' fragment thus obtained were used to replace the KSI gene in vector pET-31b(+) to yield pHTPI3 vector (5'-EcoR I-polyhedrin-Xho I-3'). See FIG. 6B.

EXAMPLE 9

Figure 7:
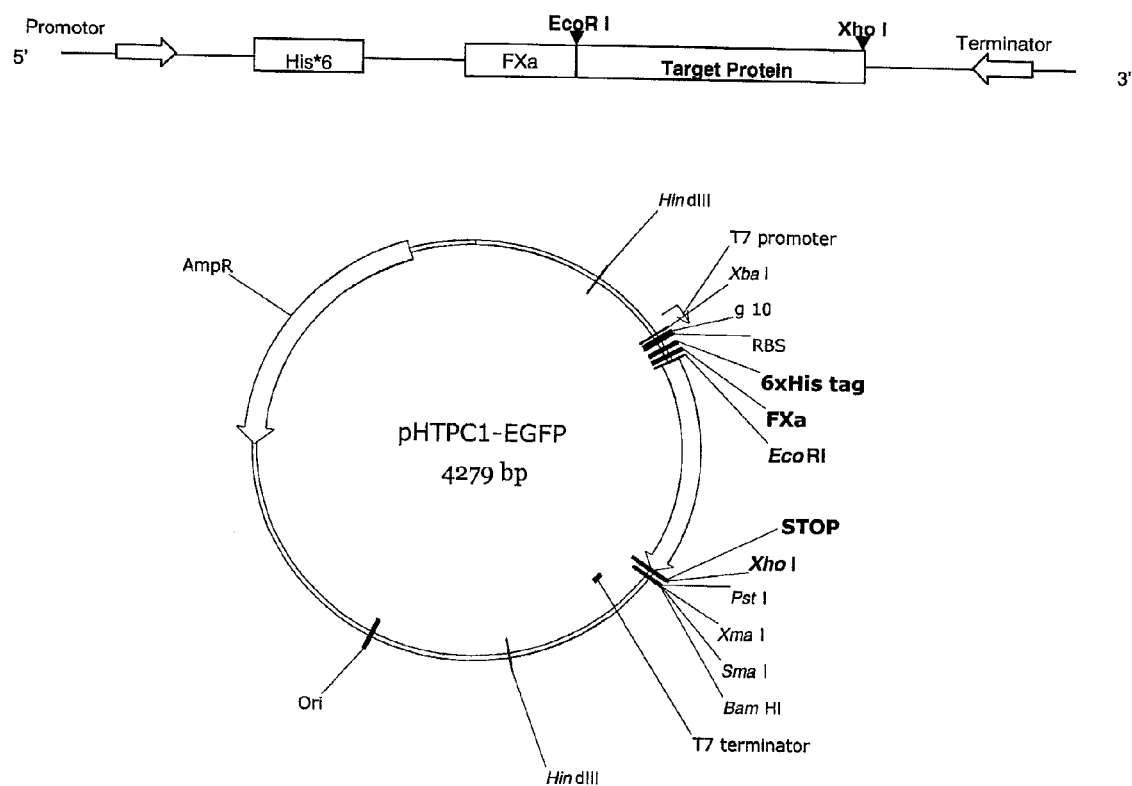
FIG. 7 is a map of expression vector pHTPC1 with EGFP gene cloned therein (6× His tags disclosed as SEQ ID NO: 71).

Construction of Expression Vectors for Expressing Tag-Cleavable Fusion Proteins in a Cell-Free System Vector pHTPC1, designed for protein expression in a cell-free system, was constructed as follows. Two pairs of primers, 5'-GGCCGCGAATTCTTAATTAAACATATG-3' (SEQ ID NO: 64) and 5'-GCG AATTCTTAATTAAAC ATATG-3' (SEQ ID NO: 65); and 5'-GTCATG TTTGACAGCTTAT-3' (SEQ ID NO: 66) and 5'-AATTGTCATGTTTG ACAGCT-TAT-3' (SEQ ID NO: 67) were used to generate a sticky-end PCR product (5'-Not I-EcoR I-EcoR I*-3') with pIVX-2.4d-1 vector as a template. The PCR product was then ligated with Not I/EcoR I-digested pIVX-2.4d-1 vector to produce pHTPC1 vector. The EGFP gene was cloned into the pHTPC1 vector via EcoR I and Xho I sites to form vector pHTPC1-EGFP (see FIG. 7).

OTHER EMBODIMENTS

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A kit comprising 2-6 expression vectors, each of which includes:
   a first nucleic acid encoding a protein tag, and
   a second nucleic acid containing (i) a nucleotide sequence that encodes a protease recognition site and (ii) one or two restriction sites identical in all of the 2-6 expression vectors for cloning a target gene that encodes a target polypeptide,
   wherein each of the expression vectors allows in a host cell production of a fusion protein including the protein tag, the protease recognition site, and the target polypeptide, which is separable from the protein tag via protease cleavage at the protease recognition site; and at least two of the expression vectors allow protein production in two different host cells, which are selected from the group consisting of an *E. coli* host cell, a yeast host cell, an insect host cell, and a mammalian host cell, and
   wherein the second nucleic acid includes the nucleotide sequence of GAGAACCTGTACGTACAG (SEQ ID NO: 1), which encodes a TEV protease recognition site and includes an SnaB I site used for cloning the target gene.

2. The kit of claim 1, wherein each of the 2-6 expression vectors allows expression of a fusion protein, which upon TEV protease cleavage, yields a polypeptide having the exact amino acid sequence encoded by the target gene.

3. The kit of claim 2, wherein the first protein tag is selected from the group consisting of hexa-His (SEQ ID NO: 71), Maltose binding protein, N-utilizing substance A, Thioredoxin, Calmodulin-binding protein, Glutathione S-transferase, and α-factor.

4. A kit comprising a first expression vector set for protein expression in a first host cell, the first expression vector set including:
   (a) a first expression vector that contains a first nucleic acid encoding a first protein tag, and a second nucleic acid containing (i) a nucleotide sequence that encodes a first protease recognition site and (ii) one or two restriction sites for cloning a target gene encoding a target polypeptide, wherein the first expression vector allows production of a fusion protein including the first protein tag, the first protease recognition site, and the target polypeptide, which is separable from the first protein tag via protease cleavage at the first protease recognition site; and
   (b) a second expression vector that contains a first nucleic acid encoding a second protein tag, and a second nucleic acid containing a restriction site and the nucleotide sequence of GAGAACCTGTACGTACAG (SEQ ID NO: 1), which encodes a TEV protease recognition site and includes an SnaB I site, the restriction site and the SnaB I site being used for cloning a target gene encoding a target polypeptide, wherein the second expression vector allows production of a fusion protein including the second protein tag, the TEV protease recognition site, and the target polypeptide, which is separable from the second protein tag via TEV protease cleavage at the TEV recognition site.

5. The kit of claim 4, wherein the two restriction sites included in the first expression vector are EcoRI and XhoI and the first protease recognition site is Factor Xa recognition site.

6. The kit of claim 5, wherein the second expression vector allows production of a fusion protein, which upon TEV protease cleavage, yields a polypeptide having the exact amino acid sequence encoded by the target gene.

7. The kit of claim 6, wherein the first protein tag is the same as the second protein tag.

8. The kit of claim 4, further comprising a second expression vector set for protein expression in a second host cell, which is different from the first host cell, the second expression vector including:
   (a) a first expression vector that contains a first nucleic acid encoding a first protein tag, and a second nucleic acid containing (i) a nucleotide sequence that encodes a first protease recognition site and (ii) one or two restriction sites for cloning a gene encoding a target polypeptide, wherein the first expression vector allows production of a fusion protein including the first protein tag, the first protease recognition site, and the target polypeptide, which is separable from the first protein tag via protease cleavage at the first protease recognition site; and (b) a second expression vector that contains a first nucleic acid encoding a second protein tag, and a second nucleic acid containing a restriction site and a nucleotide sequence of GAGAACCTGTACGTACAG (SEQ ID NO: 1), which encoding a TEV protease recognition site and includes an SnaB I site, the first restriction site and the SnaB I site being used for cloning a target gene encoding a target polypeptide, wherein the second expression vector allows production of a fusion protein including the second protein tag, the TEV recognition site, and the target polypeptide, which is separable from the second protein tag via TEV protease cleavage at the TEV recognition site.

9. The kit of claim 8, wherein the two restriction sites included in the first expression vector are EcoRI and XhoI and the first protease recognition site is Factor Xa recognition site.

10. The kit of claim 8, wherein the second expression vector allows production of a fusion protein, which upon TEV protease cleavage, yields a polypeptide having the exact amino acid sequence encoded by the target gene.

11. A kit comprising 2-6 expression vectors, each of which comprises:
a first nucleic acid encoding a protein tag, and
a second nucleic acid containing (i) a nucleotide sequence that encodes a protease recognition site and (ii) one or two restriction sites identical in all of the 2-6 expression vectors for cloning a target gene that encodes a target polypeptide, wherein each of the expression vectors allows in a host cell production of a fusion protein including the protein tag, the protease recognition site, and the target polypeptide, which is separable from the protein tag via protease cleavage at the protease recognition site; and at least two of the expression vectors allow protein production in two different host cells, which are selected from the group consisting of an *E. coli* host cell, a yeast host cell, a baculovirus host cell, and a mammalian host cell.

12. The kit of claim 11, wherein the protein tag is selected from the group consisting of hexa-His (SEQ ID NO: 71), Maltose binding protein, N-utilizing substance A, Thioredoxin, Calmodulin-binding protein, Glutathione S-transferase, and α-factor.

13. The kit of claim 11, wherein the protease recognition site is selected from the group consisting of the recognition sites of Thrombin, Factor Xa, and Tobacco etch virus (TEV) protease.

14. The kit of claim 11, wherein the two restriction sites are EcoRI and XhoI.

15. The kit of claim 14, wherein the protease recognition site is Factor Xa.

16. The kit of claim 15, wherein the protein tag is selected from the group consisting of hexa-His (SEQ ID NO: 71), Maltose binding protein, N-utilizing substance A, Thioredoxin, Calmodulin-binding protein, Glutathione S-transferase, and α-factor.

* * * * *